(12) United States Patent
Okanojo et al.

(10) Patent No.: US 8,569,047 B2
(45) Date of Patent: Oct. 29, 2013

(54) MICROBIAL DETECTION APPARATUS, MICROBIAL DETECTION METHOD, AND SAMPLE CONTAINER USED THEREIN

(75) Inventors: Masahiro Okanojo, Kokubunji (JP); Hideyuki Noda, Kokubunji (JP); Noe Miyashita, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 302 days.

(21) Appl. No.: 12/714,185

(22) Filed: Feb. 26, 2010

(65) Prior Publication Data

US 2010/0216183 A1 Aug. 26, 2010

(30) Foreign Application Priority Data

Feb. 26, 2009 (JP) ................... 2009-044648

(51) Int. Cl.
*C12M 1/00* (2006.01)
*C12M 3/00* (2006.01)
*C12M 1/34* (2006.01)

(52) U.S. Cl.
USPC .............. 435/288.7; 435/287.1; 435/283.1; 435/288.5; 435/308.1

(58) Field of Classification Search
USPC ........................................... 435/283.1–309.4
See application file for complete search history.

(56) References Cited

U.S. PATENT DOCUMENTS

| | | | |
|---|---|---|---|
| 4,278,084 A * | 7/1981 | Pope, Jr. .................... | 604/406 |
| 5,185,127 A | 2/1993 | Vonk | |
| 5,766,868 A | 6/1998 | Seto | |
| 6,375,854 B2 * | 4/2002 | Beplate ........................ | 210/767 |
| 7,201,782 B2 * | 4/2007 | Devos ............................. | 48/61 |
| 2001/0000067 A1 | 3/2001 | Beplate | |
| 2003/0042211 A1 | 3/2003 | Beplate | |
| 2005/0148091 A1 * | 7/2005 | Kitaguchi et al. ............ | 436/164 |

(Continued)

FOREIGN PATENT DOCUMENTS

CN 101137429 A 3/2008
EP 0 563 858 A1 10/1993

(Continued)

OTHER PUBLICATIONS

John Blamire, Size and Shape of Bacteria, 2000, Science at a Distance©, http://www.brooklyn.cuny.edu/bc/ahp/CellBio/SaS/SandS.html ).*

(Continued)

*Primary Examiner* — Nathan Bowers
*Assistant Examiner* — Lydia Edwards
(74) *Attorney, Agent, or Firm* — Mattingly & Malur, PC

(57) ABSTRACT

The sample container has a two-layer membrane filter comprising a first layer as an upper layer serving as a hydrophilic membrane filter and a hydrophobic membrane filter as an underlying second layer capable of filtering an aqueous solution without the use of a wetting agent and by means of a formed negative pressure. Using this sample container, a large amount of an aqueous sample solution is filtered by means of a negative pressure formed by a suction portion to capture microbes in the aqueous sample solution by the hydrophilic membrane filter. Then, the negative pressure is restored to normal pressure, and a microbial dissolution solution is then added to the membrane filter to retain the microbial dissolution solution for a given time on the hydrophobic membrane filter. Then, the microbial dissolution solution is dispensed to a reaction container containing a luminescent reagent, and luminescence is detected to detect the microbes.

9 Claims, 16 Drawing Sheets

(56) References Cited

U.S. PATENT DOCUMENTS

| | | | |
|---|---|---|---|
| 2006/0127967 A1* | 6/2006 | Touitou et al. | 435/32 |
| 2006/0269929 A1* | 11/2006 | Hall et al. | 435/6 |
| 2009/0057225 A1 | 3/2009 | Krause et al. | |
| 2009/0253181 A1* | 10/2009 | Vangbo et al. | 435/91.1 |

FOREIGN PATENT DOCUMENTS

| | | |
|---|---|---|
| EP | 0841403 A2 | 5/1998 |
| JP | 62-138185 A | 6/1987 |
| JP | 3-118473 A | 5/1991 |
| JP | 08-23962 A | 1/1996 |
| JP | 9-317792 A | 12/1997 |
| JP | 10-215859 A | 8/1998 |
| JP | 11-137293 A | 5/1999 |
| JP | 2008-096324 A | 4/2008 |
| JP | 2008-136423 A | 6/2008 |
| JP | 2008-249628 A | 10/2008 |
| JP | 2008-268-19 A | 11/2008 |
| JP | 2008-268019 A | 11/2008 |
| JP | 2009-131186 A | 6/2009 |
| JP | 2009-139115 A | 6/2009 |
| WO | 01/59157 A2 | 8/2001 |
| WO | 02/065125 A1 | 8/2002 |

OTHER PUBLICATIONS

T. Sakakibara et al., Enumeration of bacterial cell numbers by amplified firefly bioluminescence without cultivation, Analytical Biochemistry 312, Jul. 8, 2002, 9 pp.

J. Lee et al., Rapid quantification of viable bacteria in water using an ATP assay, Oct. 2001, 2 pp.

Journal: Beer Science and Technology, 2004, (2) Title: Application of a membrane filter in micro-inspection.

Chinese Office Actions received in CN2010101242334 dated Jul. 10, 2012 and Dec. 26, 2012.

CN Office Action in CN App. No. 2010101242334, dated Apr. 17, 2013.

JP Office Action in JP App. No. 2009-044648, dated May 8, 2012.

JP Final Office Action in JP App. No. 2009-044648, dated Oct. 9, 2012.

* cited by examiner

FIG. 14A-a    FIG. 14A-b    FIG. 14A-c
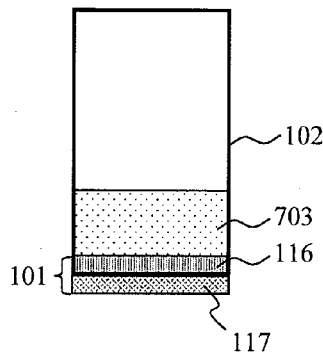 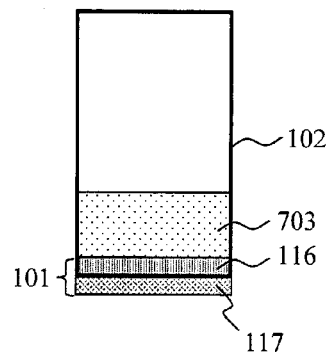 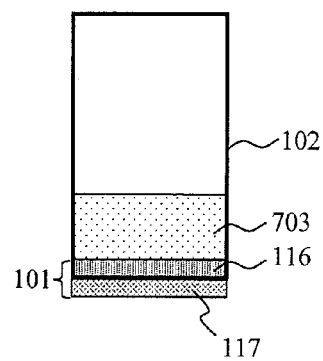
FIG. 14B-a    FIG. 14B-b    FIG. 14B-c
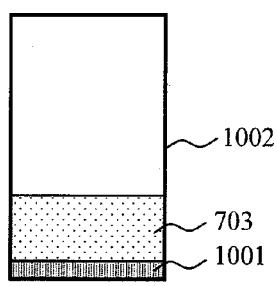 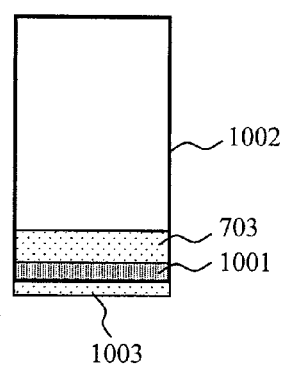 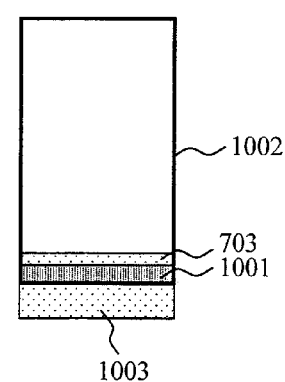

MICROBIAL DETECTION APPARATUS, MICROBIAL DETECTION METHOD, AND SAMPLE CONTAINER USED THEREIN

CLAIM OF PRIORITY

The present application claims priority from Japanese patent application JP 2009-044648 filed on Feb. 26, 2009, the content of which is hereby incorporated by reference into this application.

BACKGROUND OF THE INVENTION

1. Field of the Invention

The present invention relates to a microbial detection apparatus, a microbial detection method, and a sample container used therein.

2. Background Art

The detection of microbes or the determination of microbial counts is practiced, for example, in pharmaceutical or food factories or regenerative medical facilities, as management for safety and health that stops the microbial contamination of products before it starts. In particular, the determination of microbial counts is conducted under the provisions of the Japanese Pharmacopoeia on products or raw materials in pharmaceutical factories as well as on air, the surface of walls or workers' gloves, etc., within pharmaceutical factories. The determination of microbial counts is also conducted in food factories with the introduction of HACCP (Hazard Analysis and Critical Control Point) and conducted as inspection of the food factories themselves or their working process on food products as well as on the surface of walls, floors, or cookware such as cutting boards and kitchen knifes.

The determination of microbial counts is generally performed by a culture method. The culture method is a microbial-count determination method which comprises: for liquid samples, directly plating the samples onto an agar plate medium or for samples in a state other than liquid, plating a liquid containing microbes washed out of the samples, onto a medium; culturing the microbes on the medium; and counting the number of formed colonies by use of the fact that one microbe forms one colony.

Another general approach is a membrane filter (MF) method by which microbial counts are determined using a membrane filter. The MF method is a determination method which comprises: filtering samples through a membrane filter to capture microbes; placing the membrane filter having the captured microbes, onto an agar plate medium and culturing the microbes thereon; and counting the number of colonies. Alternatively, a method without the use of culture comprises: spraying a mist of an ATP extraction reagent for extracting adenosine triphosphate (ATP) from within microbes and a luminescent reagent containing luciferase and luciferin, onto a membrane filter having the captured microbes; photographing, using a CCD (charge coupled device) camera, the bright points of luminescence generated through the luciferase-luciferin reaction with ATP; and determining microbial counts (Japanese Patent Application No. 9-317792).

SUMMARY OF THE INVENTION

Conventional culture methods involve plating microbe-containing samples onto an agar plate medium and therefore have the problem of the highest sample amount being limited to approximately 1 mL. Accordingly, the methods have difficulty in determining the microbial counts for a large amount of samples containing a small number of microbes. Also, the methods disadvantageously require a 24- to 72-hour culture to obtain determination results. As a result, pharmaceutical or food products, live cells, and the like must be shipped only after the obtainment of determination results. This gives rise to a large loss of safety, efficiency, and economy. Thus, it has been demanded to reduce the time required for the determination of microbial counts.

In conventional MF methods, nutrients in a medium may hardly be distributed to microbes if intimate contact is not completely provided between a membrane filter having the captured microbes and the medium, due to air entering therebetween. In such a case, the growth rates of the microbes are not constant, disadvantageously resulting in varying sizes of colonies and reduced determination precision. The MF methods involve spraying an ATP extraction reagent onto microbes captured in the membrane filter. If the sprayed extraction reagent is diluted with samples or buffer solutions infiltrated in the membrane filter or if the microbial cell walls are strong enough to resist the given amount of the extraction reagent, extraction efficiency is reduced, resulting in reduced determination sensitivity.

An object of the present invention is to rapidly, highly precisely, highly sensitively, and conveniently detect and determine a small number of microbes contained in a large amount of a sample.

We have intended to provide an apparatus and a method for rapidly, highly precisely, highly sensitively, and conveniently detecting and determining a small number of microbes contained in a large amount of a sample, and have therefore attempted to develop an apparatus and a method by which a microbe-containing sample is filtered through a membrane filter; the microbes are dissolved in a sufficient amount of a microbial dissolution solution; and the microbes are detected based on luminescent or fluorescent reaction with microbe-derived biological materials as an index. During the course of this process, we have first found the problems shown below.

When the microbe-containing sample is filtered through a porous hydrophilic membrane filter, microbes having a diameter evidently larger than the pore size of the membrane filter are captured on the surface of the membrane filter. By contrast, microbes having a diameter close to the pore size of the membrane filter have been found to infiltrate into the membrane filter and be thereby captured therein. When a microbial dissolution reagent (e.g., ATP extraction reagent) is added onto the membrane filter having the microbes thus captured therewithin, the microbes have been found to be dissolved within the membrane filter such that most of the extracted biological materials (e.g., ATP) remain in the membrane filter. When the extracted ATP on the membrane filter is transferred therefrom together with the ATP extraction reagent in such a state to a container containing a bioluminescent reagent (e.g., luciferase/luciferin) and subjected to luminescence measurement, luminescence intensity has been found to be decreased due to ATP remaining as a loss in the membrane filter, resulting in reduced determination performance.

Thus, we have also attempted a method which comprises adding the extraction reagent onto the hydrophilic membrane filter and leaving it standing or stirring the solution for a given time to liberate ATP from within the membrane filter. However, in such a case, ATP has been found to penetrate through the membrane filter and drop off, together with the extraction reagent, before being liberated from within the membrane filter, resulting in difficult liberation.

We have further attempted a method using a hydrophobic membrane filter impermeable to aqueous solutions, instead of a hydrophilic membrane filter, to prevent the ATP extraction reagent from penetrating through the membrane filter and dropping off. First, the hydrophobic membrane filter must be infiltrated with a wetting agent (e.g., alcohols such as methyl alcohol and ethyl alcohol or ethers such as diethyl ether) for filtering a microbe-containing aqueous sample solution through the hydrophobic membrane filter. However, the wetting agent dissolves or damages microbes. In addition, elution of the wetting agent from the membrane filter during filtration deteriorates filtration performance. Thus, this approach which involves infiltrating the hydrophobic membrane filter with a wetting agent prior to filtration has been found to be difficult to use in microbial detection/quantification and microbial viability determination.

The present invention has been achieved to solve these problems found by us and the problems of the conventional techniques. We have found that even using a hydrophobic membrane filter, an aqueous sample solution can be filtered, depending on its pore size, without the use of a wetting agent by forming a negative pressure below the membrane filter, and have also found that the extraction reagent neither penetrates through the membrane filter nor drops off when normal pressure is provided below the hydrophobic membrane filter. The filtration of an aqueous solution through the hydrophobic membrane filter is achieved with a pore size equal to or larger than a certain size. Certain microbes having a size smaller than the pore size are hardly captured. Thus, we have developed a two-layer membrane filter which is capable of filtering a large amount of an aqueous solution, capturing microbes, and retaining a microbial dissolution solution, by providing, on the hydrophobic membrane filter, a porous hydrophilic membrane filter with a very small pore size for capturing microbes.

A microbial detection apparatus of the present invention comprises: a sample container comprising, in the bottom, a two-layer membrane filter comprising a first layer as an upper layer serving as a hydrophilic membrane filter and a hydrophobic membrane filter as an underlying second layer capable of filtering an aqueous solution without the use of a wetting agent and by means of a formed negative pressure; and a suction portion provided below the two-layer membrane filter in the sample container. The hydrophilic membrane filter as the first layer of the two-layer membrane filter is responsible for capturing microbes, while the hydrophobic membrane filter as the second layer is responsible for retaining a reagent.

According to the present invention, a large amount of an aqueous sample solution can be filtered through the hydrophilic membrane filter as the first layer and the hydrophobic membrane filter as the second layer by means of a negative pressure formed by the suction portion. Thus, microbes in the aqueous sample solution can be captured by the hydrophilic membrane filter as the first layer without being dissolved or damaged. Then, the negative pressure is restored to normal pressure, and a microbial dissolution solution is then added to the membrane filter. As a result, the hydrophobic membrane filter as the second layer can retain thereon the microbial dissolution solution for a given time to prevent the microbial dissolution solution from penetrating through the membrane filter and dropping off. According to the present invention, the microbes captured by the hydrophilic membrane filter as the first layer can be dissolved, and microbe-derived biological materials within the hydrophilic membrane filter as the first layer can be liberated into the solution on the hydrophilic membrane filter as the first layer.

The hydrophilic membrane filter as the first layer has a pore size of preferably 0.05 μm to 0.65 μm. The hydrophobic membrane filter as the second layer has a pore size of preferably 0.8 μm to 80 μm. The hydrophilic membrane filter as the first layer having a pore size set to 0.05 μm to 0.65 μm can reliably capture microbes. The hydrophobic membrane filter as the second layer having a pore size set to 0.8 μm to 80 μm can filter an aqueous sample solution without the use of a wetting agent and by means of a formed negative pressure and can retain thereon a microbial dissolution solution under normal pressure restored from the negative pressure.

A microbial detection method of the present invention comprises: adding a first reagent for degrading an extra-microbial biological material, to an aqueous sample solution to degrade the extra-microbial biological material; suction-filtering the aqueous sample solution through the two-layer membrane filter to capture microbes by the hydrophilic membrane filter as the first layer while removing the first reagent and foreign substances contained in the aqueous sample solution; then adding thereto a second reagent for extracting biological materials within the microbes, and retaining the second reagent on the hydrophobic membrane filter as the second layer to extract the biological materials from the microbes and liberate the biological materials from within the hydrophilic membrane filter as the first layer; and allowing the liberated biological materials to act on a third reagent reactive thereto, followed by quantitative measurement of the microbes. In this context, the second reagent used is a reagent that does not infiltrate into the hydrophobic membrane filter.

The present invention provides a microbial detection apparatus and a microbial detection method which are capable of easily filtering a large amount of an aqueous sample solution, reliably dissolving microbes, and easily eluting, from the membrane filter, biological materials extracted from the microbes. The present invention also provides a microbial detection apparatus and a microbial detection method which achieve highly sensitive, highly precise, rapid, and convenient microbial viability determination and live cell quantification without the use of a culture and without the need of experience.

BRIEF DESCRIPTION OF THE DRAWINGS

FIG. 14A (14A-a to 14A-c) is a diagram illustrating a measurement experiment on the ability of the two-layer membrane filter to retain a microbial dissolution solution.

FIG. 14B (14B-a to 14B-c) is a diagram illustrating a measurement experiment on the ability of a single-layer hydrophilic membrane filter to retain a microbial dissolution solution.

DETAILED DESCRIPTION OF THE PREFERRED EMBODIMENTS

Hereinafter, the embodiments of the present invention will be described with reference to the drawings. However, the present invention is not limited to the description below by any means.

Example 1

(Microbial Detection Apparatus and Method)

Figure 1:
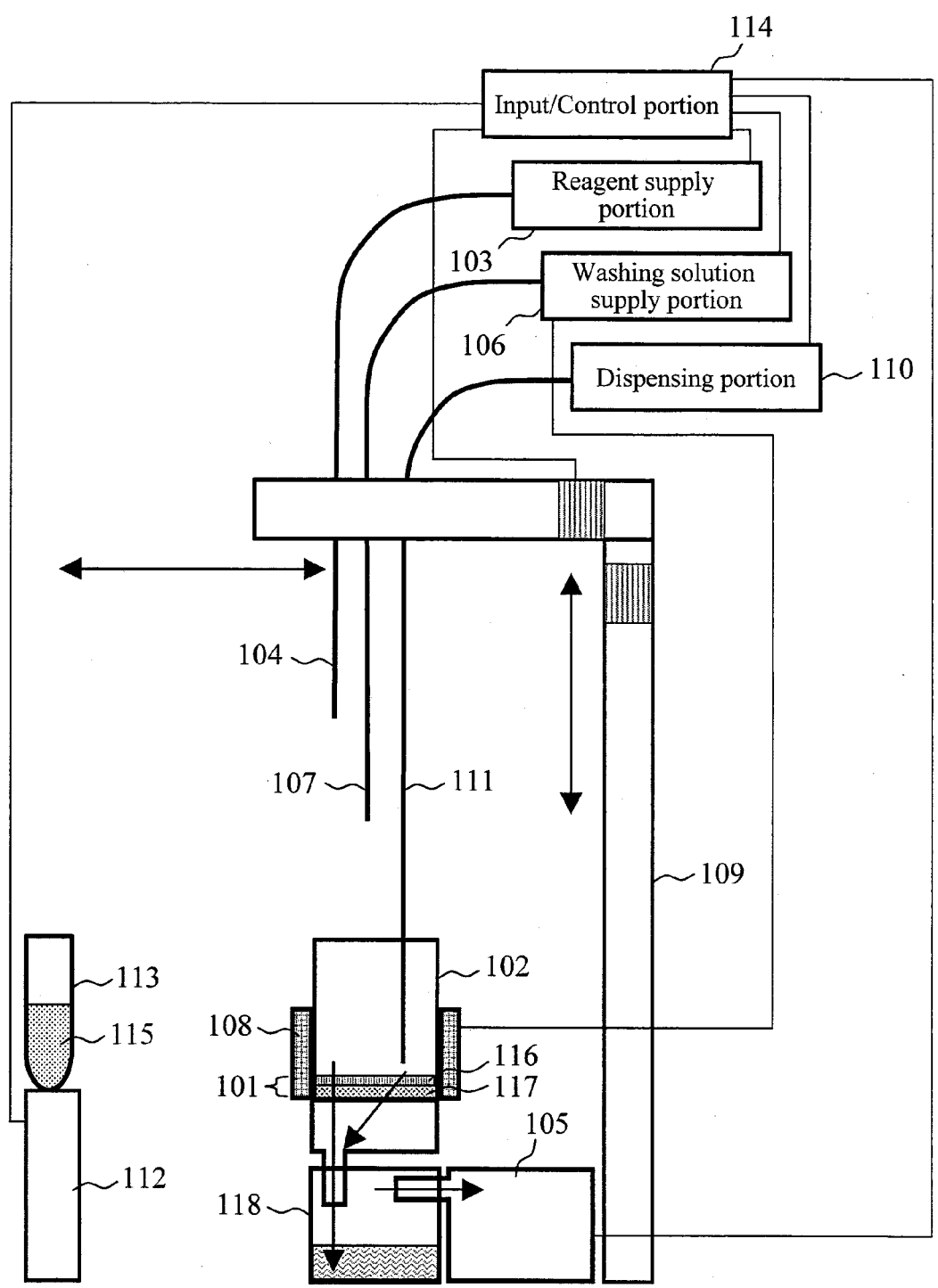
FIG. 1 is a schematic diagram showing a partial cross section of a microbial detection apparatus according to an embodiment of the present invention.

FIG. 1 is a schematic diagram showing a partial cross section of a microbial detection apparatus according to an embodiment of the present invention. The microbial detection apparatus comprises a container 102 comprising a two-layer membrane filter 101 in the bottom, a reagent supply portion 103, a pipe 104 for reagent supply, a suction portion 105, a washing solution supply portion 106, a pipe 107 for washing solution supply, a heating portion 108, an arm 109, a dispensing portion 110, a pipe 111 for dispensing, a detection portion 112, a reaction container 113, and an input/control portion 114. The input/control portion 114 performs centralized control of the operation of each portion in the apparatus. The container 102 is detachable/attachable from/to the apparatus. The reaction container 113 contains a luminescent reagent 115.

The two-layer membrane filter 101 has a first layer as an upper layer serving as a hydrophilic membrane filter 116 and a second layer as a lower layer serving as a hydrophobic membrane filter 117. The hydrophilic membrane filter 116 as the first layer has a pore size set to 0.05 μm to 0.65 μm for reliably capturing microbes. It also has a thickness set to 7 μm to 200 μm. Of course, the hydrophilic membrane filter 116 may have a thickness smaller or larger than this range. However, a membrane filter thinner than this range has weak mechanical strength and is presumably broken during filtration. Alternatively, a membrane filter thicker than this range presumably allows a large amount of a solution to remain therein, with which various reagents added thereafter are diluted. Thus, the thickness is preferably 7 μm to 200 μm. The hydrophobic membrane filter 117 as the second layer has a pore size set to 0.8 μm to 80 μm for reliably filtering an aqueous solution. It also has a thickness set to 7 μm to 800 μm. Of course, the hydrophobic membrane filter 117 may have a thickness smaller or larger than this range. However, a membrane filter thinner than this range has weak mechanical strength and is presumably broken during filtration. Alternatively, a membrane filter thicker than this range presumably requires time for suction filtration. Thus, the thickness is preferably 7 μm to 800 μm.

Figure 2:
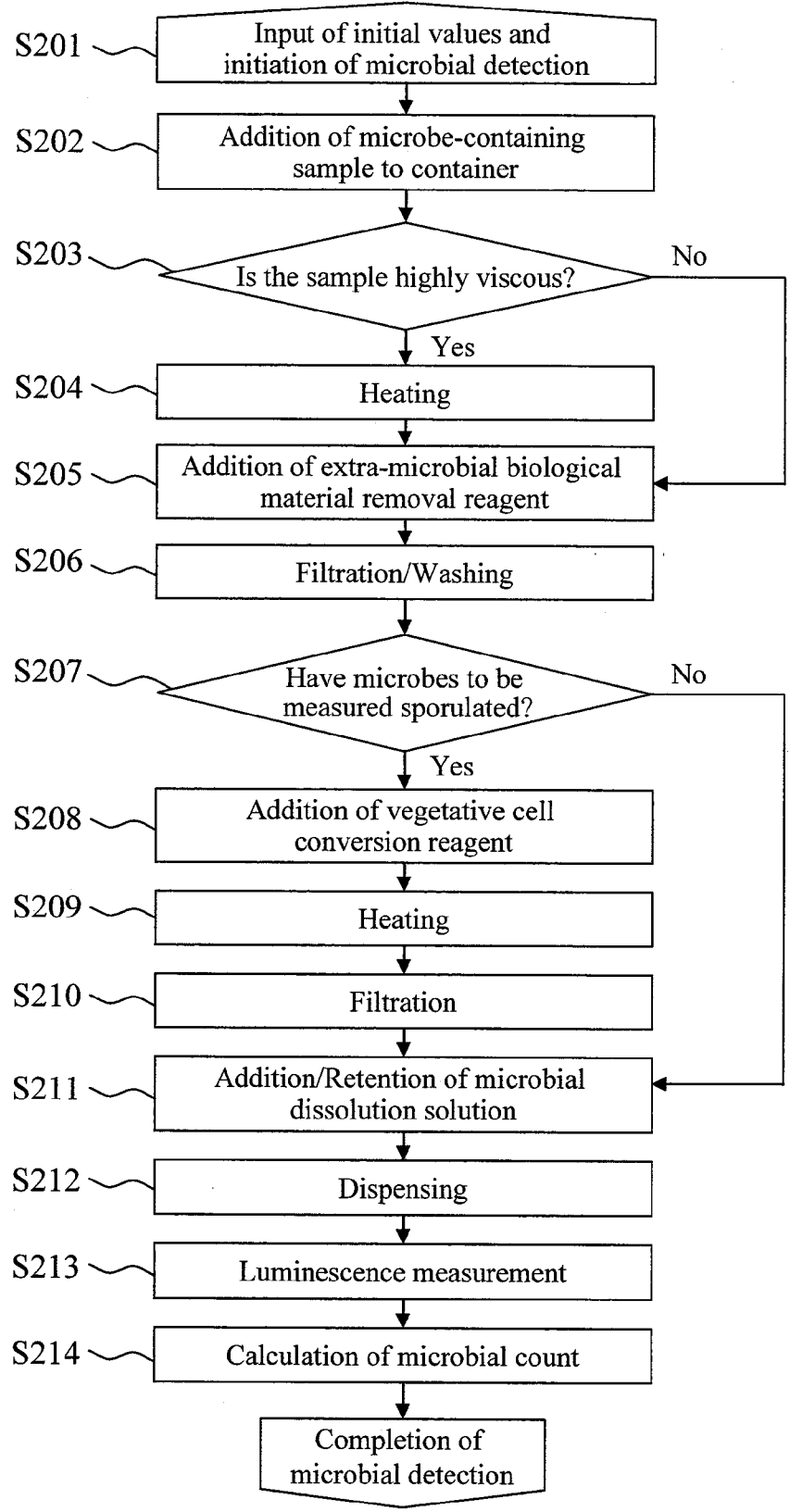
FIG. 2 is a flowchart showing procedures of a microbial detection process.

FIG. 2 is a flowchart showing procedures of a microbial detection process using the microbial detection apparatus shown in FIG. 1. FIGS. 3 to 6 respectively show alternative embodiments of the microbial detection apparatus of the present invention, which will be described below together therewith.

The container 102 comprising the two-layer membrane filter 101 in the bottom is loaded in the apparatus. First, initial values as to the high or low viscosity of a sample or whether or not *Bacillus subtilis* in a spore form can be measured are input to the input/control portion 114, and microbial detection is initiated (S201). An aqueous sample solution containing microbes to be measured is added to the container 102 (S202). When the aqueous sample solution is judged in step 203 as having high viscosity, the input/control portion 114 drives the heating portion 108 to heat the aqueous sample solution for promoting quick filtration (S204). When the sample viscosity input in the step 201 is low, the process goes to step 205 without the heating step.

Next, an extra-microbial biological material degradation reagent is supplied from the reagent supply portion 103 through the pipe 104 for reagent supply to the aqueous sample solution in the container 102 (S205). The extra-microbial biological material degradation reagent used is, for example, ATPase, DNase (DNA: deoxyribonucleic acid), or RNase (RNA: ribonucleic acid).

Figure 3:
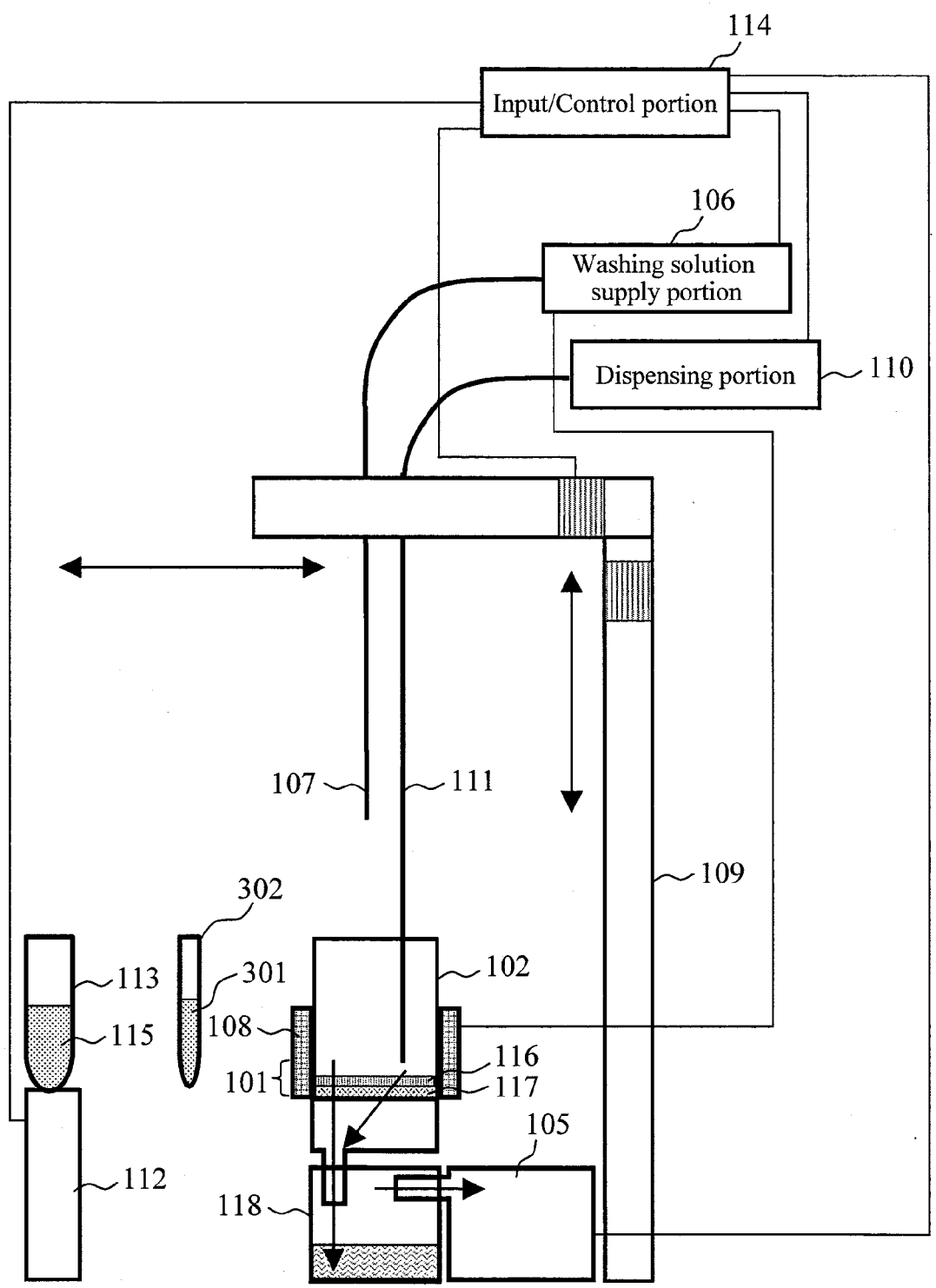
FIG. 3 is a schematic diagram showing a partial cross section of a microbial detection apparatus according to an embodiment of the present invention.

As shown in FIG. 3, the microbial detection apparatus may comprise, instead of a reagent supply portion, a reagent reservoir 302 containing various reagents 301. In such a case, the microbial detection apparatus may comprise a dispensing portion 110 which dispenses an extra-microbial biological material degradation reagent in the reagent reservoir 302 through the pipe 111 for dispensing to the aqueous sample solution. The apparatus having the reagent supply portion 103 shown in FIG. 1 is suitable in uses for measuring a large number of samples per day, and the apparatus having the reagent reservoir shown in FIG. 3 is suitable in uses for measuring a small number of samples.

Next, the aqueous sample solution in the container 102 is filtered through the two-layer membrane filter 101 by means of a negative pressure formed by the suction portion 105. In this filtration, microbes in the aqueous solution are captured by the hydrophilic membrane filter as the first layer, while the biological material degradation reagent or residual biological materials flow into a waste liquid portion 118 for removal. Then, a washing solution is supplied from the washing solution supply portion 106 for the purpose of washing the two-layer membrane filter 101 (S206). When the aqueous sample solution has high viscosity, a washing solution may be supplied from the washing solution supply portion 106 through the pipe 107 for washing solution supply for the purpose of reducing the viscosity. Likewise, for the purpose of reducing the viscosity, the washing solution may be heated by the heating portion 108 and then added to the aqueous sample solution.

Next, when the microbes to be measured are judged in step 207 as having sporulated, a vegetative cell conversion reagent is added thereto from the reagent supply portion 103 after the filtration (S208). The vegetative cell conversion reagent used is, for example, combination of alanine, glucose, and phosphoric acid or may be a liquid medium. For the microbial detection apparatus comprising the reservoir 302 for various reagents shown in FIG. 3, a vegetative cell conversion reagent in the reagent reservoir 302 is dispensed by the dispensing portion 110 to the aqueous sample solution. The vegetative cell conversion reagent may also be heated by the heating portion 108 for promoting the conversion to vegetative cells (S209). Furthermore, the solution may be filtered for the purpose of removing the vegetative cell conversion reagent (S210). When the judgment in the step 207 is No, the process goes to step 211 without the procedures of the steps 208 to 210.

Next, a microbial dissolution solution is added from the reagent supply portion 103 to retain the microbial dissolution solution on the two-layer membrane filter 101 (S211). The microbial dissolution solution used is, for example, benzalkonium chloride, trichloroacetic acid, or a Tris buffer. For the microbial detection apparatus comprising the reservoir 302 for various reagents shown in FIG. 3, a microbial dissolution solution in the reagent reservoir 302 is dispensed by the dispensing portion 110 to the aqueous sample solution.

Next, the microbial dissolution solution on the two-layer membrane filter 101 in the container 102 is aspirated through the pipe 111 for dispensing of the dispensing portion 110, and the arm 109 is driven to move the pipe 111 for dispensing to above the reaction container 113 of the detection portion 112 such that the microbial dissolution solution is transferred to the reaction container 113 (S212). The reaction container 113 contains a luminescent reagent 115, which in turn reacts with biological materials (e.g., ATP, luminol, or alkaline phosphatase) contained in the microbial dissolution solution to generate luminescence. The luminescent reagent 115 used is, for example, luciferase/luciferin. Alternatively, substrates for peroxidase or alkaline phosphatase may be used. In this case, animal cells can also be detected.

Figure 4:
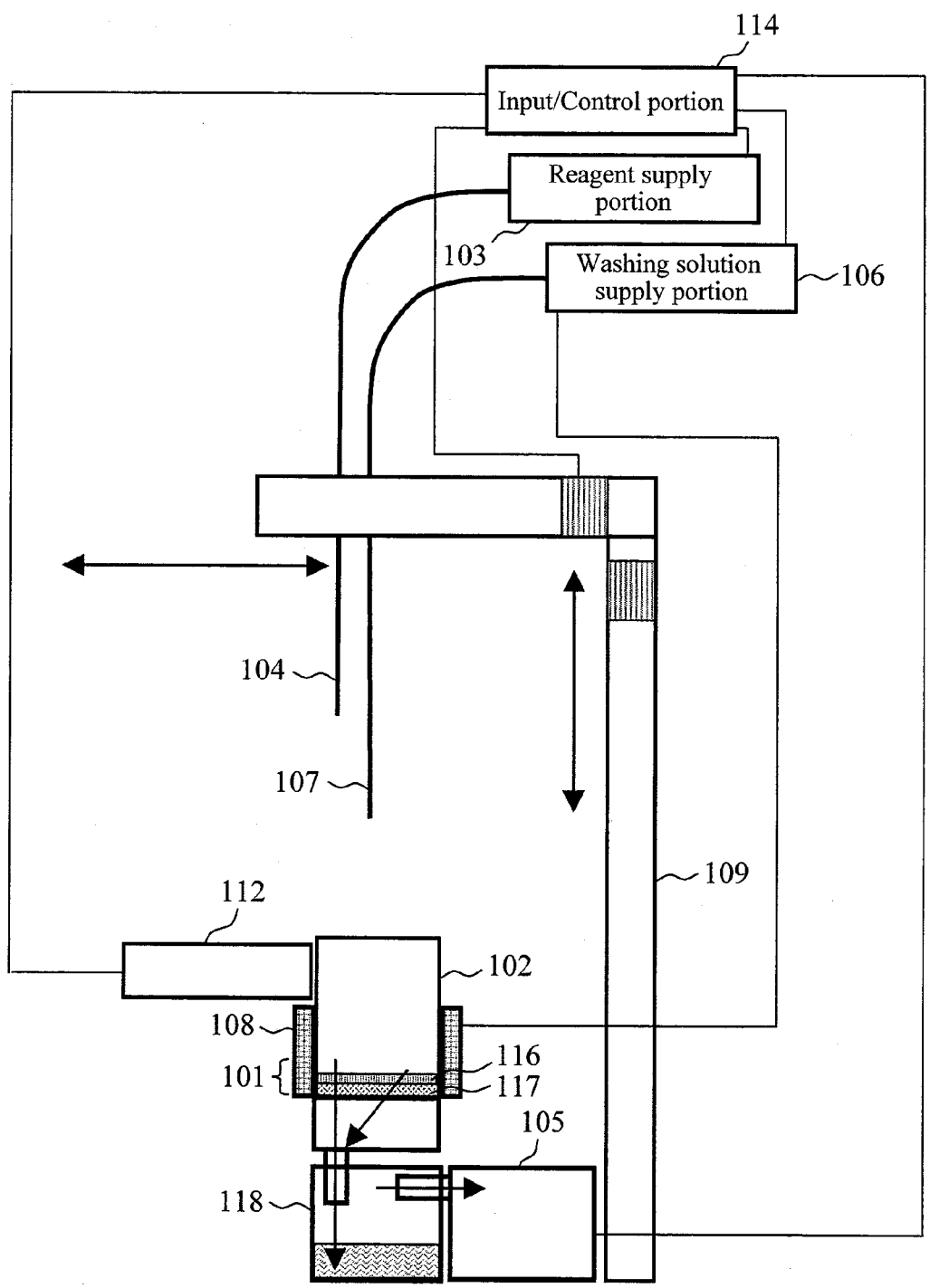
FIG. 4 is a schematic diagram showing a partial cross section of a microbial detection apparatus according to an embodiment of the present invention.
Figure 5:
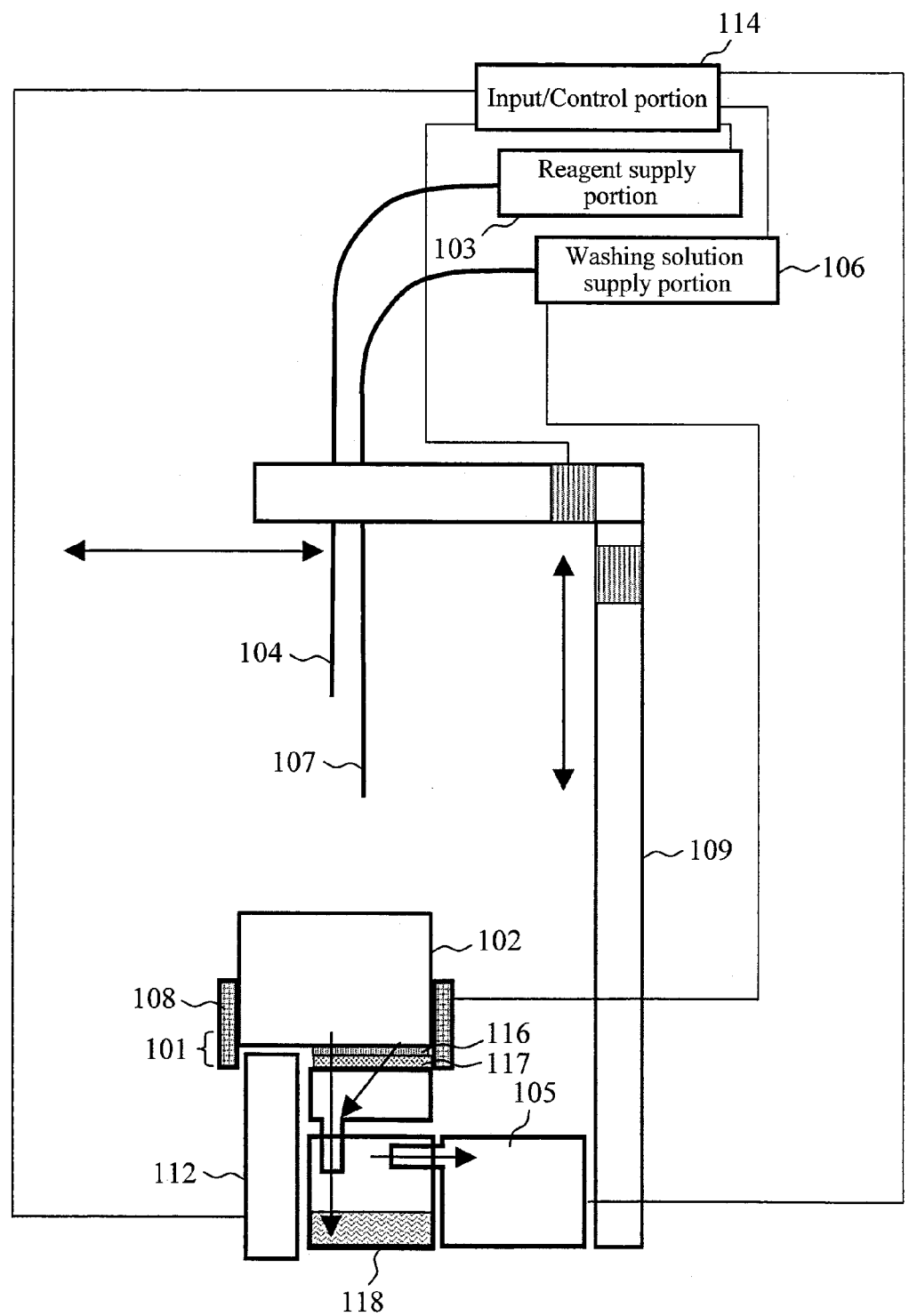
FIG. 5 is a schematic diagram showing a partial cross section of a microbial detection apparatus according to an embodiment of the present invention.
Figure 6:
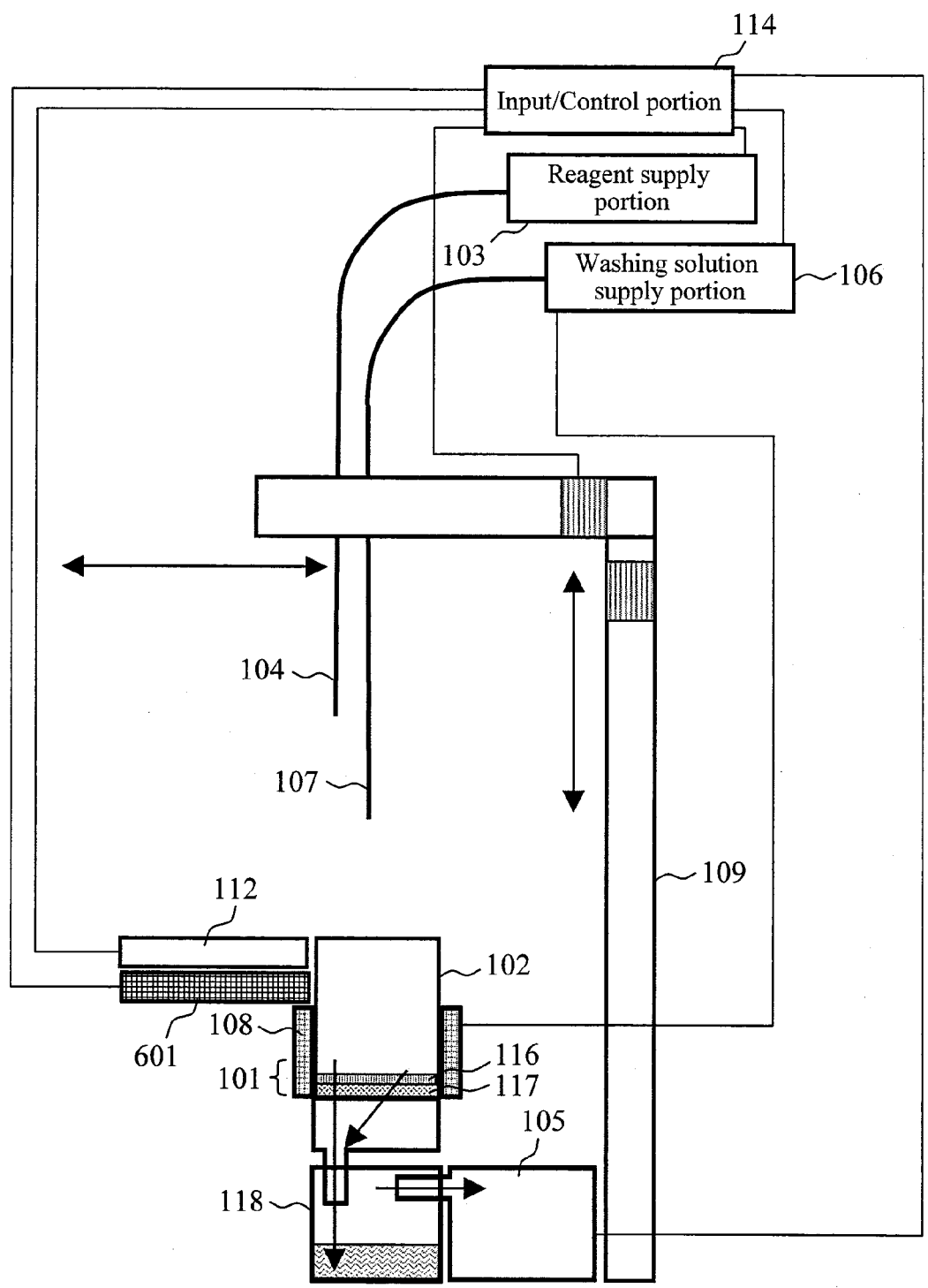
FIG. 6 is a schematic diagram showing a partial cross section of a microbial detection apparatus according to an embodiment of the present invention.

As in the embodiments shown in FIGS. 4 and 5, the microbial detection apparatus may comprise the detection portion 112 on the side of or below the container 102. In such a case, luminescence may be generated by supplying a luminescent reagent by the reagent supply portion 103 directly onto the two-layer membrane filter 101 in the container 102. In the embodiment of the microbial detection apparatus shown in FIG. 5, a container used comprises a two-layer membrane filter 101 placed not all over the bottom but in the partial region thereof and has a transparent region in the bottom. The detection portion 112 is disposed to face the transparent region in the bottom of the container and detects luminescence generated through luminescent reaction from the solution in the container. Alternatively, as in the embodiment of the apparatus shown in FIG. 6, the microbial detection apparatus may comprise an excitation light irradiation portion 601. In such a case, fluorescence may be generated by irradiating biological materials (e.g., DNA, RNA, or NAD (nicotinamide adenine dinucleotide)) with excitation light from the excitation light irradiation portion 601 without the use of a luminescent reagent.

The generated luminescence or fluorescence is detected by the detection portion 112 (S213), and microbial counts are calculated based on the detected luminescence or fluorescence intensity (S214) to complete microbial detection.

When the process shown in FIG. 2 goes from the step 207 to the step 211 without the procedures of the steps 208 to 210, followed by luminescence measurement in the step 213, the number of vegetative cells contained in the sample can be detected. Alternatively, when the procedures from the steps 208 to 214 are performed after the step 206, the number of non-vegetative cells can be detected. Thus, the numbers of vegetative cells and non-vegetative cells contained in the sample can be differentiated therebetween and detected by detecting the number of vegetative cells by the process without the steps 208 to 210 and then repeating the procedures from the steps 208 to 214.

Example 2

(Microbial Detection Experiment 1: *E. Coli*)

*E. coli* detection sensitivity was compared between the container comprising the two-layer membrane filter according to the present invention and a container comprising a conventional hydrophilic membrane filter.

Two containers equipped with a membrane filter were prepared, one of which was the container 102 comprising the two-layer membrane filter 101 in the bottom and the other of which was a container comprising only a hydrophilic membrane filter in the bottom.

Referring to FIG. 7 (7A and 7B), an example of how to mount the two-layer membrane filter into the bottom of the container will be described. The two-layer membrane filter 101 comprises a first layer as an upper layer serving as a hydrophilic membrane filter 116 and a second layer as a lower layer serving as a hydrophobic membrane filter 117. The hydrophilic membrane filter 116 used was an MF-Millipore membrane filter (Nihon Millipore Ltd.) having a pore size of 0.45 µm, a thickness of 150 µm, and porosity of 79% and was processed into 0.5 cm in diameter. The hydrophilic membrane filter may be a Durapore or Isopore membrane filter (Nihon Millipore Ltd.) instead. The hydrophobic membrane filter 117 used was a Mitex membrane filter (Nihon Millipore Ltd.) having a pore size of 10 µm and was processed into 0.5 cm in diameter. The hydrophobic membrane filter may be a polypropylene prefilter (Nihon Millipore Ltd.) having a pore size of 30 µm instead. Alternatively, the hydrophobic membrane filter may be made of a material such as nylon, polytetrafluoroethylene, hydrophobic polyvinylidene fluoride, polyethylene, polysiloxane, polycarbonate, polysulfone, polyamide, or glass fiber and may be a membrane filter having a pore size of 0.8 µm to 80 µm or a membrane filter having a mesh structure with a pitch size of 1 µm to 59 µm.

Figure 7A:
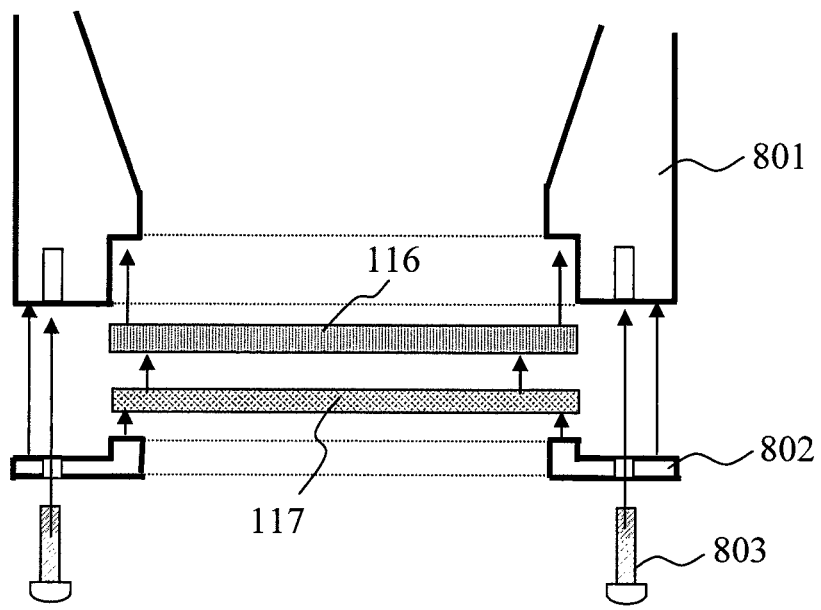
FIG. 7 (7A and 7B) is a diagram showing an example of how to mount a two-layer membrane filter into the bottom of a container.
Figure 7B:
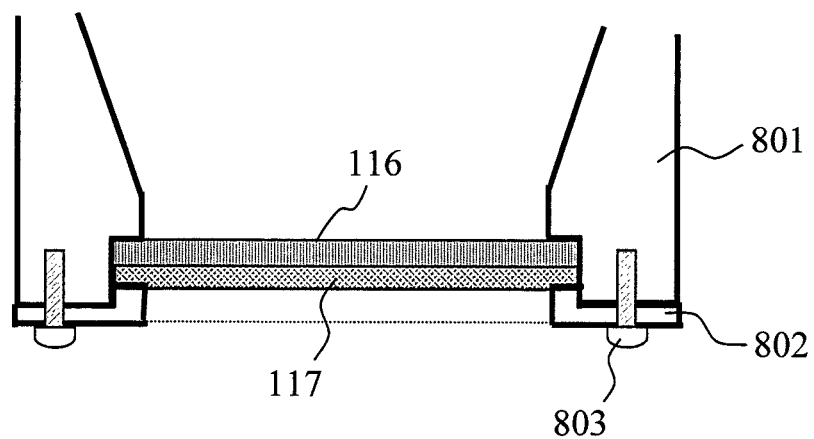
Figure 8A:
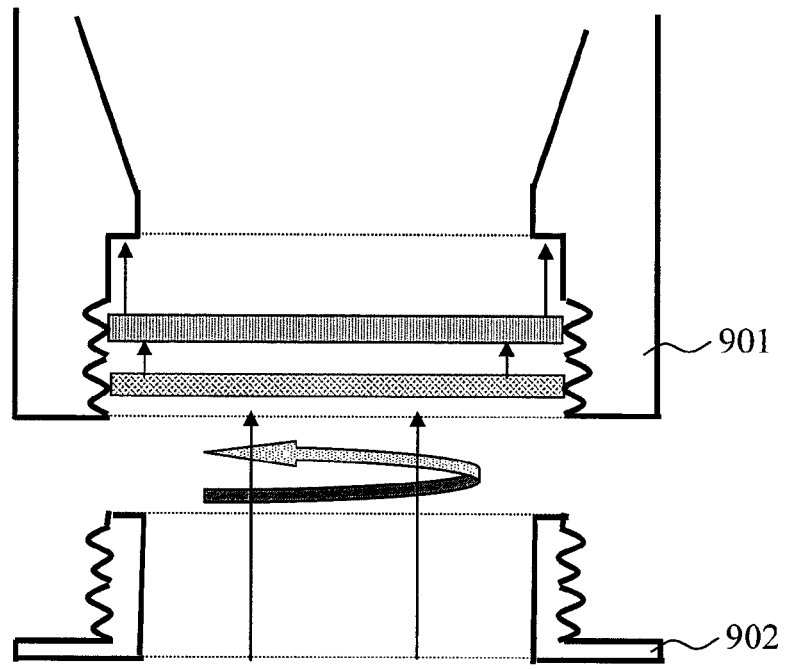
FIG. 8 (8A and 8B) is a diagram showing an example of how to mount a two-layer membrane filter into the bottom of a container.
Figure 8B:
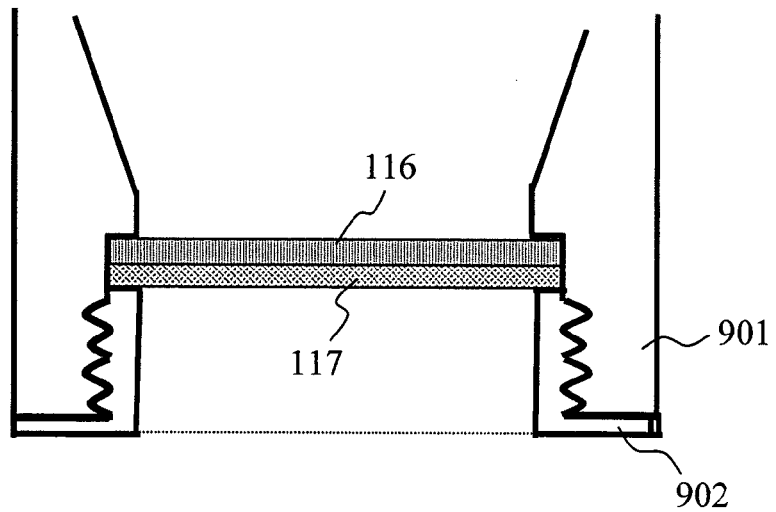

As shown in FIG. 7A, the processed hydrophilic membrane filter 116 was overlaid on the processed hydrophobic membrane filter 117, and the resulting filter was mounted to a mounting portion provided in a bottom 801 of the container 102. The outer edge of the filter was supported by an annular cap 802 and secured with a screw 803 as shown in FIG. 7B to complete assembly. Alternatively, the filter may be secured using a screwed cap. For example, as shown in FIG. 8A, the processed hydrophilic membrane filter 116 is overlaid on the processed hydrophobic membrane filter 117, and the resulting filter may be inserted between a screwed bottom 901 of the container 102 and a screwed annular cap 902 and secured with the bottom 901 and the cap 902 as shown in FIG. 8B for assembly. In this context, a gap may be formed between the hydrophilic membrane filter as the first layer and the hydrophobic membrane filter as the second layer.

Figure 10A:
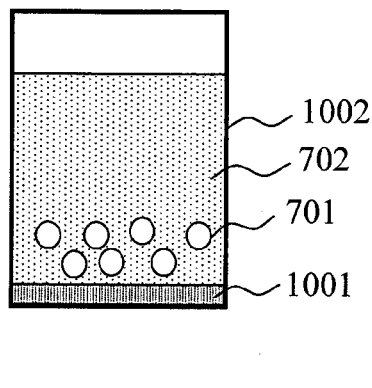
FIG. 10 (10A to 10D) is a schematic diagram showing the intermediate process of a detection method using a single-layer hydrophilic membrane filter.
Figure 10B:
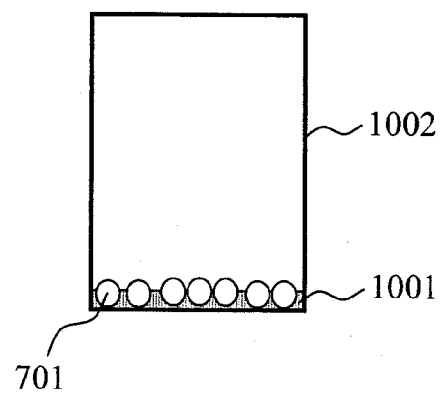
Figure 10C:
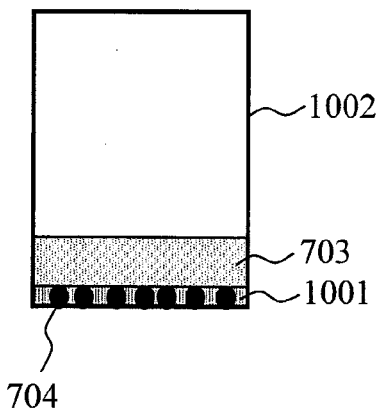

The container comprising only the hydrophilic membrane filter, which has the same container structure thereas, was a container 1002 equipped with a single-layer hydrophilic membrane filter 1001 instead of a two-layer membrane filter, as shown in an abbreviated form in FIG. 10A. The single-layer hydrophilic membrane filter 1001 used was an MF-Millipore membrane filter (Nihon Millipore Ltd.) having a pore size of 0.45 μm, a thickness of 150 μm, and porosity of 79% and was processed into 0.5 cm in diameter.

FIG. 9 (9A to 9D) is a schematic diagram showing the intermediate process of a detection method using the container comprising the two-layer membrane filter according to the present invention. FIG. 10 (10A to 10D) is a schematic diagram showing the intermediate process of a detection method using the container comprising the single-layer hydrophilic membrane filter.

E. coli was used as the microbe to be measured. E. coli 701 was suspended in a phosphate buffer (pH 7.4) (Invitrogen Corp.) for adjusting the number of E. coli to 20 to 2000 individuals/10 mL to prepare an E. coli suspension 702.

Figure 9A:
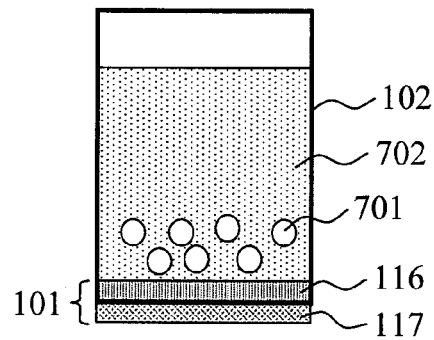
FIG. 9 (9A to 9D) is a schematic diagram showing the intermediate process of a detection method using the two-layer membrane filter according to the present invention.
Figure 9B:
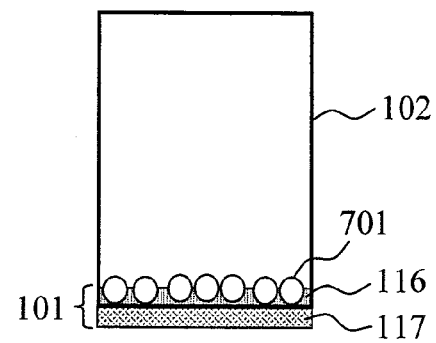
Figure 9C:
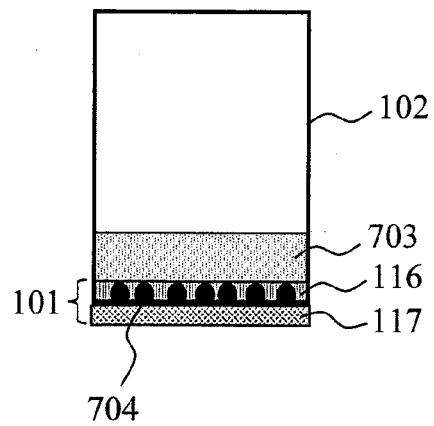

As shown in FIGS. 9A and 10A, 10 mL of the E. coli suspension 702 was first added onto each of the two-layer membrane filter 101 and the single-layer hydrophilic membrane filter 1001. Next, 10 μL of an ATP elimination solution included in Lucifer HS Set (Kikkoman Corp.) was added thereto as an extra-microbial biological material removal reagent. Subsequently, as shown in FIG. 11A, a suction port 1101 of the suction portion 105 was connected to below the two-layer membrane filter. As shown in FIG. 11B, a negative pressure is formed to filter the E. coli suspension and the ATP elimination solution. Likewise, through the single-layer hydrophilic membrane filter, the E. coli suspension and the ATP elimination solution were filtered. FIGS. 9B and 10B respectively show a state after the filtration. After the filtration, 200 μL of an ATP extraction solution included in the Lucifer HS Set (Kikkoman Corp.) was added thereto as a microbial dissolution solution 703 to extract ATP molecules 704 from the E. coli 701, as shown in FIGS. 9C and 10C.

Figure 9D:
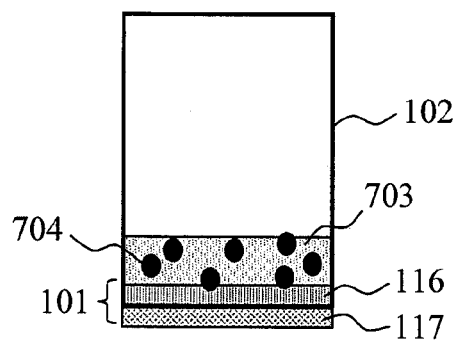
Figure 10D:
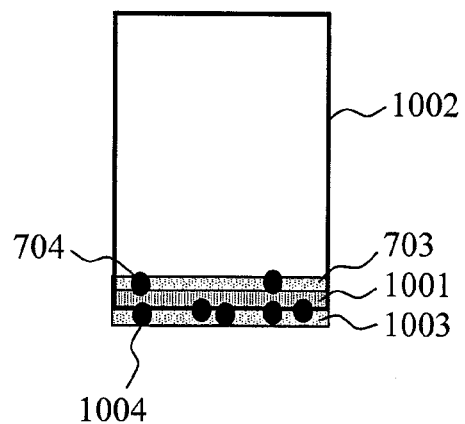
Figure 11A:
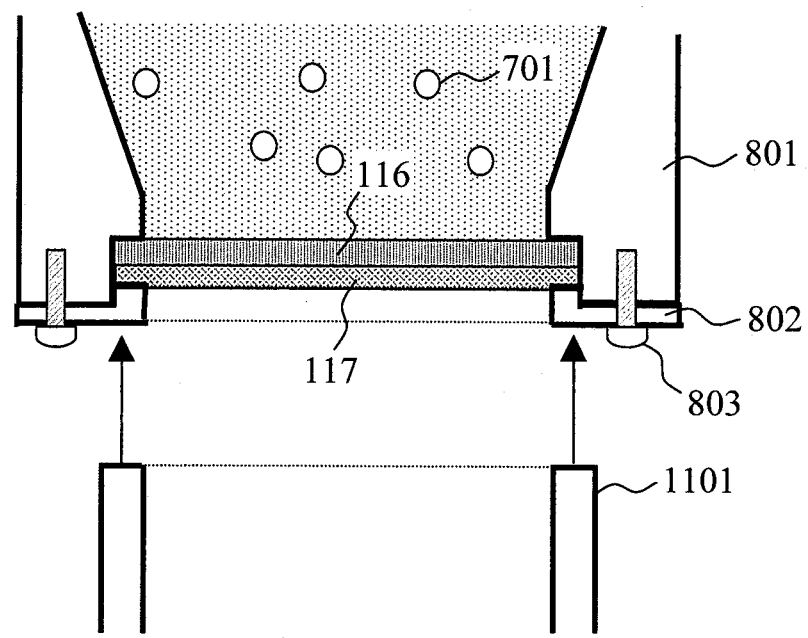
FIG. 11 (11A and 11B) is a diagram illustrating suction filtration.
Figure 11B:
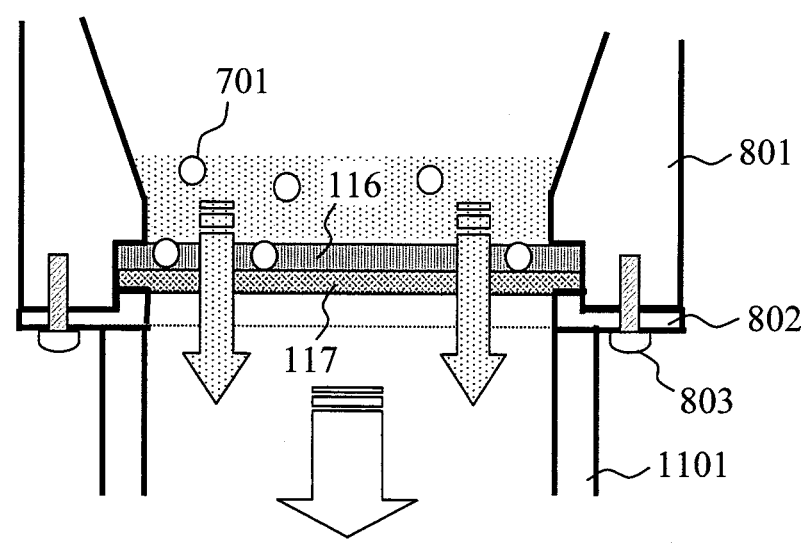

While left standing, the microbial dissolution solution 1003 penetrated through the single-layer hydrophilic membrane filter 1001 and dropped off as shown in FIG. 10D. On the other hand, no change was observed in the two-layer membrane filter 101 as shown in FIG. 9D.

Figure 12:
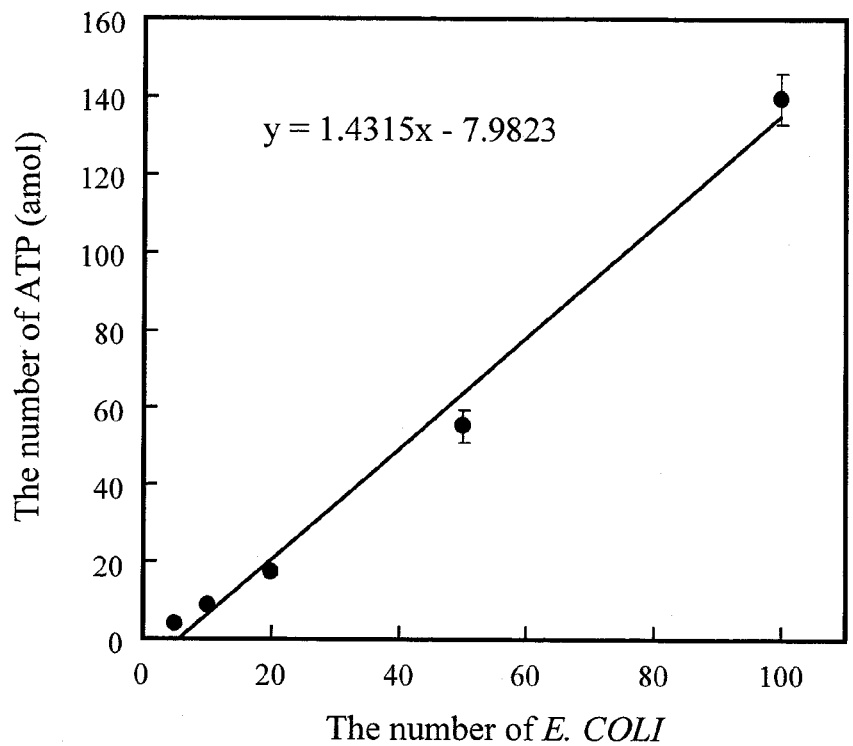
FIG. 12 is a diagram showing the relationship between the number of *E. coli* in the abscissa and the number of ATP obtained using the two-layer membrane filter.

10 μL of the microbial dissolution solution 703 remaining on each of the two-layer membrane filter 101 and the single-layer hydrophilic membrane filter 1001 was dispensed using the dispensing portion 110 to a luminescent reagent 115 (included in the Lucifer HS set (Kikkoman Corp.)) contained in the reaction container 113 placed on the detection portion 112. The luminescence intensity was calculated as the number of ATP. The results obtained using the two-layer membrane filter 101 were plotted in a diagram with the number of ATP as the ordinate against the number of E. coli as the abscissa, as shown in FIG. 12.

When the container comprising the two-layer membrane filter was used, the number of ATP and the number of E. coli exhibited a quantitative linear relation (y=1.4315x−7.9823) in which the number of ATP molecules was 1.4 amol on average per E. coli. By contrast, when the container comprising the single-layer hydrophilic membrane filter was used, ATP molecules could not be detected from less than 100 individuals of E. coli, and the number of ATP was 1 amol per 100 individuals of E. coli. Thus, the two-layer membrane filter 101 exhibited a value about 100 times higher than that of the single-layer hydrophilic membrane filter 1001.

This result may be because in the container comprising the single-layer hydrophilic membrane filter, the single-layer hydrophilic membrane filter cannot retain thereon the microbial dissolution solution, and therefore, the microbial dissolution solution 1003 penetrates through the single-layer hydrophilic membrane filter and drops off together with E. coli-derived ATP molecules 1004. As a result, the E. coli-derived ATP molecules 1004 were not eluted into the microbial dissolution solution on the single-layer hydrophilic membrane filter 1001 (FIG. 10D).

On the other hand, in the container comprising the two-layer membrane filter, the two-layer membrane filter 101 can retain thereon the microbial dissolution solution 703, and therefore, the microbial dissolution solution 703 neither penetrates through the two-layer membrane filter 101 nor drops off together with the E. coli-derived ATP molecules 704. Moreover, the ATP molecules 704 extracted from E. coli within the hydrophilic membrane filter 116 as the first layer are eluted with time into the microbial dissolution solution on the two-layer membrane filter 101 (FIG. 9D).

The microbial detection apparatus of the present invention could measure one E. coli highly sensitively, highly precisely, rapidly, and conveniently. The same effect is also obtained for bacteria such as a coliform group and Staphylococcus, yeast such as Saccharomyces cerevisiae, and fungi such as Aspergillus niger.

Example 3

(Microbial Detection Experiment 2: Bacillus subtilis in Spore Form)

Detection sensitivity of Bacillus subtilis in a spore form was compared between the container comprising the two-layer membrane filter according to the present invention and a container comprising a conventional hydrophilic membrane filter.

Two containers equipped with a membrane filter were prepared, one of which was the container 102 comprising the two-layer membrane filter 101 and the other of which was a container comprising only a hydrophilic membrane filter. The container structures and the structures in which the two-layer membrane filter or the single-layer hydrophilic membrane filter is mounted on the container are as described in FIGS. 7 and 8 (8A and 8B).

The two-layer membrane filter 101 comprised a first layer as an upper layer serving as a hydrophilic membrane filter 116 and a second layer as a lower layer serving as a hydrophobic membrane filter 117. The hydrophilic membrane filter 116 used was an MF-Millipore membrane filter (Nihon Millipore Ltd.) having a pore size of 0.45 μm, a thickness of 150 μm, and porosity of 79% and was processed into 0.5 cm in diameter. The hydrophilic membrane filter may be a Durapore or Isopore membrane filter (Nihon Millipore Ltd.) instead. The hydrophobic membrane filter 117 used was a Mitex membrane filter (Nihon Millipore Ltd.) having a pore size of 10 μm and was processed into 0.5 cm in diameter. The hydrophobic membrane filter may be a polypropylene prefilter (Nihon Millipore Ltd.) having a pore size of 30 μm instead. Alternatively, the hydrophobic membrane filter may be made of a material such as nylon, polytetrafluoroethylene, hydrophobic polyvinylidene fluoride, polyethylene, polysiloxane, polycarbonate, polysulfone, polyamide, or glass fiber and may be a membrane filter having a pore size of 0.8 μm to 80 μm or a membrane filter having a mesh structure with a pitch size of 1 μm to 59 μm.

The single-layer hydrophilic membrane filter mounted in the container comprising only the hydrophilic membrane filter was an MF-Millipore membrane filter (Nihon Millipore Ltd.) having a pore size of 0.45 μm, a thickness of 150 μm, and porosity of 79% and was processed into 0.5 cm in diameter.

Bacillus subtilis in a spore form was used as the microbe to be measured. Bacillus subtilis was suspended in a 10% w/v gelatin solution+phosphate buffer (pH 7.4) (Invitrogen Corp.) to prepare a highly viscous Bacillus subtilis suspension having 2000 individuals of *Bacillus subtilis*/10 mL. 100 mM alanin+100 mM glucose+phosphate buffer (pH 7.4) was used as a vegetative cell conversion reagent. An ATP elimination solution included in the Lucifer HS Set (Kikkoman Corp.) was used as an extra-microbial biological material removal reagent. An ATP extraction solution included in the Lucifer HS Set (Kikkoman Corp.) was used as a microbial dissolution solution.

The microbial detection apparatus shown in FIG. 3 was used in this measurement. In the present Example, a touch panel display was used for input to the input/control portion 114. Alternatively, the input/control portion 114 used may be, for example, a laptop computer, a desktop computer, or an input button combined with a display and a USB (universal serial bus) memory for input/output.

First, the *Bacillus subtilis* suspension is highly viscous because it contains gelatin. The *Bacillus subtilis* suspension also contains sporulated bacteria. Therefore, the information about the high viscosity of the *Bacillus subtilis* suspension and the sporulated bacteria contained therein was input using the input/control portion 114. Subsequently, the input/control portion 114 directed the apparatus to initiate microbial detection. The apparatus performs detection process according to the steps shown in FIG. 2.

10 mL of the *Bacillus subtilis* suspension was added onto each of the two-layer membrane filter and the single-layer hydrophilic membrane filter (S202). The input/control portion 114 judged the *Bacillus subtilis* suspension in step 203 as having high viscosity based on the input information and controlled the heating portion 108 to heat the *Bacillus subtilis* suspension at 40° C. for reducing the viscosity (S204).

10 μL of the ATP elimination solution was added to the *Bacillus subtilis* suspension (S205), and the *Bacillus subtilis* suspension and the ATP elimination solution were filtered through each of the two-layer membrane filter 101 and the single-layer hydrophilic membrane filter by means of a negative pressure formed by the suction portion 105 (S206).

After the filtration, the input/control portion 114 judged the solution in step 207 as containing sporulated bacteria based on the input information. For converting the spores to vegetative cells, 1 mL of the vegetative cell conversion reagent was added onto each of the two-layer membrane filter 101 and the single-layer hydrophilic membrane filter (S208). The vegetative cell conversion reagent was heated at 40° C. or 45° C. for approximately 1 hour by the heating portion 108 to promote the conversion of the spores to vegetative cells (S209). After 1 hour, the vegetative cell conversion reagent penetrated through the single-layer hydrophilic membrane filter and dropped off. By contrast, the vegetative cell conversion reagent was retained on the two-layer membrane filter 101 and therefore filtered again (S210).

Subsequently, 200 μl of the ATP extraction reagent was added thereto and left standing for 10 minutes (S211). While left standing, the ATP extraction solution penetrated through the single-layer hydrophilic membrane filter and dropped off. By contrast, no change was observed in the two-layer membrane filter 101. 10 μL of the ATP extraction solution remaining on each of the two-layer membrane filter 101 and the single-layer hydrophilic membrane filter was dispensed by the dispensing portion 110 to a luminescent reagent 115 contained in the reaction container 113 placed on the detection portion 112 (S212). The detection portion 112 detected generated luminescence (S213), and the input/control portion 114 calculated the number of ATP from the luminescence intensity (S214).

Figure 13:
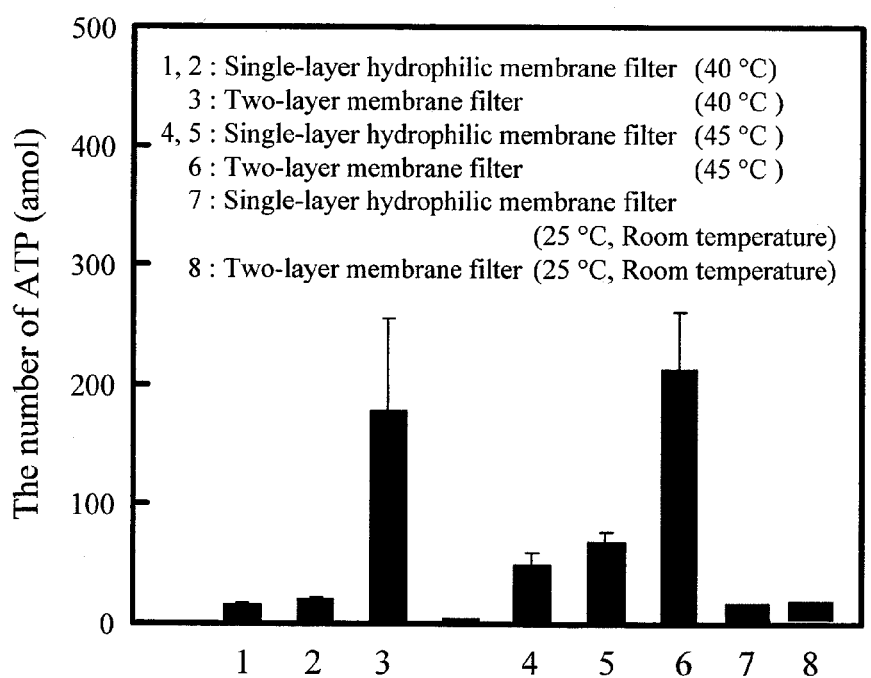
FIG. 13 is a diagram showing the number of ATP detected under various conditions.

The results of detecting the number of ATP are shown in FIG. 13. When the single-layer hydrophilic membrane filter was used, the number of ATP was approximately 10 amol per 100 individuals of *Bacillus subtilis*. By contrast, when the two-layer membrane filter 101 was used, the number of ATP was an estimate of approximately 200 amol, which was 20 times higher than that of the single-layer hydrophilic membrane filter. This result may be because the single-layer hydrophilic membrane filter cannot retain thereon the ATP extraction solution, and therefore, the ATP extraction solution penetrates through the single-layer hydrophilic membrane filter and drops off together with *Bacillus subtilis*-derived ATP molecules. As a result, the *Bacillus subtilis*-derived ATP molecules were not eluted into the solution on the single-layer hydrophilic membrane filter. On the other hand, the two-layer membrane filter 101 can retain thereon the ATP extraction solution, and therefore, the ATP extraction solution neither penetrates through the two-layer membrane filter 101 nor drops off together with the *Bacillus subtilis*-derived ATP molecules. Thus, the *Bacillus subtilis*-derived ATP molecules within the hydrophilic membrane filter 116 as the first layer could be eluted with time into the solution on the two-layer membrane filter 101.

When the vegetative cell conversion reagent was not heated by the heating portion 108 (25° C., room temperature in FIG. 13), the number of ATP was approximately 10 amol per 100 individuals of *Bacillus subtilis*.

Thus, the microbial detection apparatus of the present invention could measure *Bacillus subtilis* highly sensitively, highly precisely, rapidly, and conveniently.

The present invention has been completed by the accumulation of various experiments. Hereinafter, the experiments on which the present invention is based will be described.

Experimental Example 1

(Examination of Hydrophobic Membrane Filter Capable of Retaining Aqueous Solution and Filtering the Aqueous Solution Under Negative Pressure)

The presence or absence of a hydrophobic membrane filter was examined, which is capable of retaining an aqueous solution and filtering the aqueous solution under negative pressure.

The pore sizes, pitch sizes, and materials of the examined hydrophobic membrane filters are shown in Table 1. The aqueous solutions used in the experiment are ultrapure water, a phosphate buffer, and a microbial dissolution solution. The phosphate buffer is 50 mM phosphoric acid/NaOH buffer, pH 7.4. The microbial dissolution solution is 0.2% benzalkonium chloride+25 mM Tricine buffer, pH 12.

TABLE 1

| Material | Pore size (μm) | Dropwise addition | | | Filtration under negative pressure | | |
|---|---|---|---|---|---|---|---|
| | | Water | Phosphate | Microbial dissolution solution | Water | Phosphate | Microbial dissolution solution |
| Polytetrafluoroethylene | 10 | Retained | Retained | Retained | Possible | Possible | Possible |
| | 3 | Retained | Retained | Retained | Possible | Possible | Possible |

TABLE 1-continued

| Material | size (μm) | Retained | Retained | Retained | Possible | Possible | Possible |
|---|---|---|---|---|---|---|---|
| | 0.45 | Retained | Retained | Retained | Impossible | Impossible | Impossible |
| Polypropylene | 80 | Retained | Retained | Retained | Possible | Possible | Possible |
| | 30 | Retained | Retained | Retained | Possible | Possible | Possible |
| | 0.6 | Retained | Retained | Retained | Difficult | Difficult | Difficult |
| Polyvinylidene fluoride | 0.45 | Retained | Retained | Retained | Impossible | Impossible | Impossible |
| | 0.22 | Retained | Retained | Retained | Impossible | Impossible | Impossible |
| | 0.1 | Retained | Retained | Retained | Impossible | Impossible | Impossible |
| Nylon | 0.8 | Retained | Retained | Retained | Possible | Possible | Possible |

| | Pitch | Dropwise addition | | | Filtration under negative pressure | | |
|---|---|---|---|---|---|---|---|
| Material | size (μm) | Water | Phosphate | Microbial dissolution solution | Water | Phosphate | Microbial dissolution solution |
| Nylon | 59 | Retained | Retained | Retained | Possible | Possible | Possible |
| | 38 | Retained | Retained | Retained | Possible | Possible | Possible |
| | 25 | Retained | Retained | Retained | Possible | Possible | Possible |
| | 10 | Retained | Retained | Retained | Possible | Possible | Possible |
| | 5 | Retained | Retained | Retained | Possible | Possible | Possible |
| | 1 | Retained | Retained | Retained | Possible | Possible | Possible |

The aqueous solutions were separately added dropwise onto each hydrophobic membrane filter to examine the ability to retain the aqueous solution (Table 1). As a result, all the aqueous solutions could be retained on the hydrophobic membrane filters made of any of the materials and neither penetrated through the membrane filter nor dropped off.

The hydrophobic membrane filters were also examined for whether or not each aqueous solution could be filtered therethrough by means of a negative pressure (Table 1). As a result, the hydrophobic membrane filters having a pore size of 0.8 μm to 80 μm were impermeable to the aqueous solutions under normal pressure and could filter the aqueous solutions under negative pressure. The hydrophobic membrane filters having a pore size of 0.6 μm or smaller hardly achieved filtration under negative pressure, and the hydrophobic membrane filters having a pore size of 0.45 μm failed to filter the aqueous solutions. In addition, the hydrophobic membrane filters having a mesh structure with a pitch size of 1 μm to 59 μm retained the aqueous solutions and could filter them under negative pressure.

Moreover, a hydrophilic membrane filter having a pore size of 0.05 μm to 0.65 μm was overlaid onto a hydrophobic membrane filter having a pore size of 0.8 μm to 80 μm or a pitch size of 1 μm to 59 μm to prepare a two-layer membrane filter. Filtration was attempted by adding aqueous solutions onto the two-layer membrane filter. As a result, the two-layer membrane filter also achieved filtration of the aqueous solutions.

Experimental Example 2

(Measurement Experiment on Ability of Two-Layer Membrane Filter to Retain Microbial Dissolution Solution)

The ability to retain a microbial dissolution solution was compared between the two-layer membrane filter and a single-layer hydrophilic membrane filter. For this purpose, two containers comprising either membrane filter in the bottom were prepared.

One of the containers was the container 102 comprising the two-layer membrane filter 101 (FIG. 14A-*a*). The two-layer membrane filter 101 comprised a first layer as an upper layer serving as a hydrophilic membrane filter 116 and a second layer as a lower layer serving as a hydrophobic membrane filter 117. The hydrophilic membrane filter 116 as the first layer used was an MF-Millipore membrane filter (Nihon Millipore Ltd.) having a pore size of 0.45 μm, a thickness of 150 μm, and porosity of 79% and was processed into 0.5 cm in diameter. The hydrophobic membrane filter 117 as the second layer used was a Mitex membrane filter (Nihon Millipore Ltd.) having a pore size of 10 μm.

The other container was a container 1002 comprising only a single-layer hydrophilic membrane filter 1001 as the hydrophilic membrane filter (FIG. 14B-*a*). The single-layer hydrophilic membrane filter 1001 used was an MF-Millipore membrane filter (Nihon Millipore Ltd.) having a pore size of 0.45 μm, a thickness of 150 μm, and porosity of 79% and was processed into 0.5 cm in diameter.

200 μL of 0.2% benzalkonium chloride+25 mM Tricine buffer, pH 12 was added as a microbial dissolution solution 703 onto each of the two-layer membrane filter 101 and the single-layer hydrophilic membrane filter 1001 and left standing for 10 minutes. After the 5- and 10-minute standing, no change was observed in the two-layer membrane filter 101 (FIGS. 14A-b and 14A-c). By contrast, the microbial dissolution solution 1003 penetrated through the single-layer hydrophilic membrane filter 1001 and dropped off, with standing time (FIGS. 14B-*b* and 14B-c).

For measuring the amount of the microbial dissolution solution 1003 that penetrated through the single-layer hydrophilic membrane filter 1001 and dropped off, weight measurement was attempted by collecting the microbial dissolution solution 1003 that penetrated through the membrane filter and dropped off. 4 minutes after the addition of the microbial dissolution solution 703, 10 mg of the microbial dissolution solution 1003 penetrated through the membrane filter and dropped off. In measurement at 6 and 8 minutes thereafter, 15 mg and 20 mg of the microbial dissolution solution 1003, respectively, penetrated through the membrane filter and dropped off. A total of 45 mg of the microbial dissolution solution 1003 was found to penetrate through the membrane filter and drop off.

On the other hand, the microbial dissolution solution neither penetrated through the two-layer membrane filter 101 nor dropped off. Instead, the total weight of the container 102 comprising the two-layer membrane filter 101 and the microbial dissolution solution 703 was measured immediately after the addition of the microbial dissolution solution 703 onto the two-layer membrane filter 101 (FIG. 14A-*a*) and after 10-minute standing (FIG. 14A-*c*), and the difference therebetween was calculated. The difference was 1 mg, demonstrating almost no change in the weight. This result indicates that the microbial dissolution solution is retained in the container 102 comprising the two-layer membrane filter.

This result demonstrated that the two-layer membrane filter can retain thereon the microbial dissolution solution.

Experimental Example 3

(Elution Experiment on ATP within Membrane Filter)

Figure 15A:
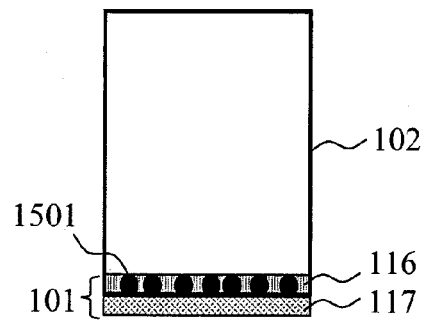
FIG. 15 (15A to 15D) is a diagram illustrating an elution experiment on ATP molecules within the two-layer membrane filter.

The amount of ATP molecules eluted from within the membrane filter was compared between the two-layer membrane filter and a single-layer hydrophilic membrane filter. For this purpose, two containers comprising either membrane filter were prepared. One of the containers was the container 102 comprising the two-layer membrane filter 101 in the bottom (FIG. 15A). The two-layer membrane filter 101 comprised a first layer as an upper layer serving as a hydrophilic membrane filter 116 and a second layer as a lower layer serving as a hydrophobic membrane filter 117. The hydrophilic membrane filter 116 as the first layer used was an MF-Millipore membrane filter (Nihon Millipore Ltd.) having a pore size of 0.45 μm, a thickness of 150 μm, and porosity of 79% and was processed into 0.5 cm in diameter. The hydrophobic membrane filter 117 as the second layer used was a Mitex membrane filter (Nihon Millipore Ltd.) having a pore size of 10 μm and was processed into 0.5 cm in diameter.

Figure 16A:
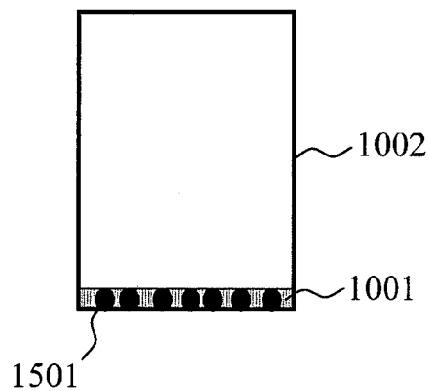
FIG. 16 (16A to 16D) is a diagram illustrating an elution experiment on ATP molecules within a single-layer hydrophilic membrane filter.

The other container was a container 1002 comprising only a single-layer hydrophilic membrane filter 1001 as the hydrophilic membrane filter in the bottom (FIG. 16A). The single-layer hydrophilic membrane filter 1001 used was an MF-Millipore membrane filter (Nihon Millipore Ltd.) having a pore size of 0.45 μm, a thickness of 150 μm, and porosity of 79% and was processed into 0.5 cm in diameter.

Lucifer ATP Standard Reagent (Kikkoman Corp.) was used as an ATP solution to prepare an ATP solution having a concentration of 20000 amol/10 mL. A luminescent reagent included in Lucifer HS Set (Kikkoman Corp.) for causing ATP/luciferase/luciferin reaction was used as a luminescent reagent 115.

Figure 15B:
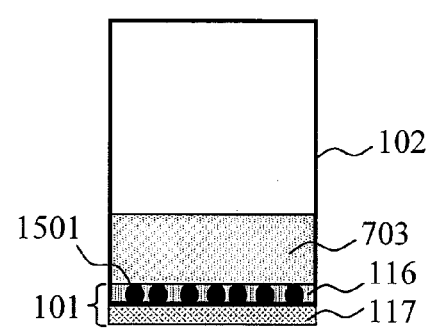
Figure 16B:
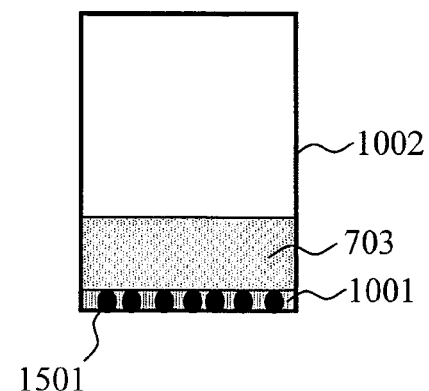

First, 10 μL of the ATP solution was added onto each of the two-layer membrane filter 101 and the single-layer hydrophilic membrane filter 1001 to infiltrate ATP molecules 1501 into each of the hydrophilic membrane filter 116 as the first layer and the single-layer hydrophilic membrane filter 1001 (FIGS. 15A and 16A). Subsequently, 200 μL of 0.2% benzalkonium chloride+25 mM Tricine buffer, pH 12 was added thereonto as a microbial dissolution solution 703 and then left standing (FIGS. 15B and 16B).

Figure 15C:
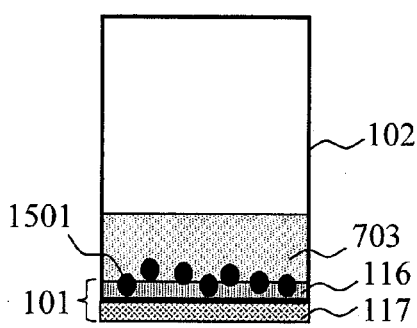
Figure 15D:
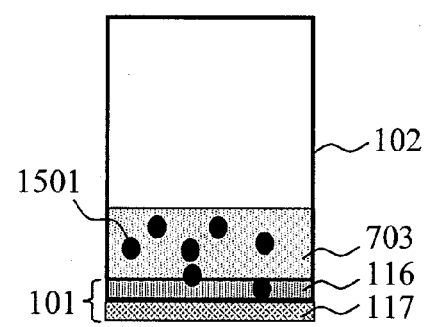
Figure 16C:
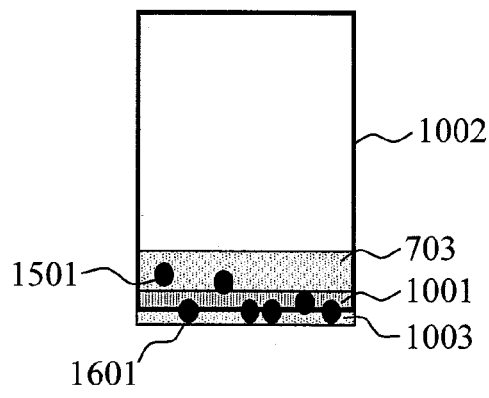
Figure 16D:
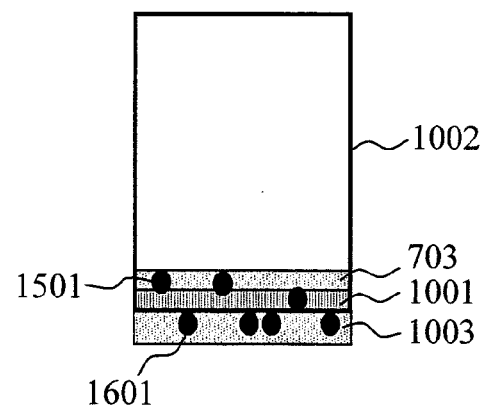

While left standing, the microbial dissolution solution 1003 penetrated through the single-layer hydrophilic membrane filter 1001 and dropped off, with time (FIGS. 16C and 16D). On the other hand, no change was observed in the two-layer membrane filter 101 (FIGS. 15C and 15D).

For quantitatively evaluating the number of ATP molecules 1601 in the microbial dissolution solution 1003 that penetrated through the single-layer hydrophilic membrane filter 1001 and dropped off as well as the number of ATP molecules 1501 liberated into the microbial dissolution solution 703 on the single-layer hydrophilic membrane filter 1001 (FIGS. 16C and 16D), a 10 μL aliquot was collected from each of the microbial dissolution solution 703 remaining on the single-layer hydrophilic membrane filter 1001 and the microbial dissolution solution 1003 that penetrated through the single-layer hydrophilic membrane filter 1001 and dropped off. The collected solution was added to the luminescent reagent 115 in the reaction container 113, and luminescence generated through the reaction was detected by the detection portion 112.

4, 6, and 8 minutes after the addition of the microbial dissolution solution 703 onto the single-layer hydrophilic membrane filter 1001, the microbial dissolution solution 1003 that penetrated through the membrane filter and dropped off exhibited luminescence intensity of approximately 20000 CPS (count per second), 25000 CPS, and 30000 CPS, respectively (FIG. 17). 20000 amol of ATP molecules existed in the single-layer hydrophilic membrane filter 1001 before penetrating through the membrane filter and dropping off, and 200 μm of the microbial dissolution solution 703 was added onto the single-layer hydrophilic membrane filter 1001. Taking this into consideration, the ATP concentration is approximately 1000 amol/10 μL when the ATP molecules 1501 are ideally distributed into the microbial dissolution solution 703. Luminescence intensity at the ATP concentration of 1000 amol/10 μL is determined in measurement to be approximately 10000 CPS. Thus, the number of ATP molecules 1601 in the microbial dissolution solution 1003 that penetrated through the single-layer hydrophilic membrane filter 1001 and dropped off was found to be 2 to 3 times larger than that obtained by the ideal distribution of ATP molecules 1501 into the microbial dissolution solution 703.

Figure 17:
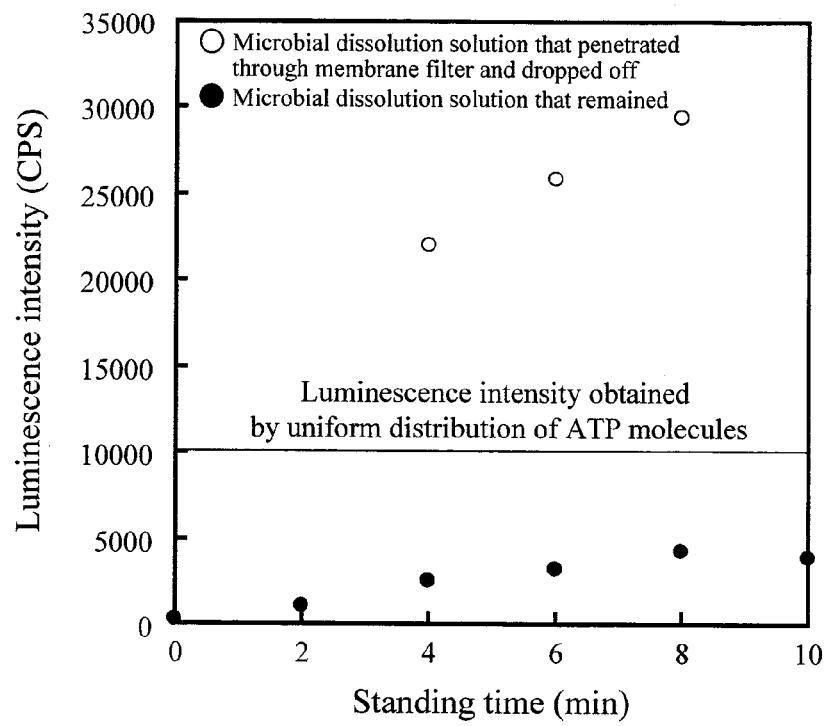
FIG. 17 is a diagram showing time-dependent change in the luminescence intensity of a microbial dissolution solution that remained on a single-layer hydrophilic membrane filter and a microbial dissolution solution that penetrated through the membrane filter and dropped off.

On the other hand, the number of ATP molecules 1501 contained in the microbial dissolution solution 703 remaining on the single-layer hydrophilic membrane filter 1001 was measured based on luminescence. As a result, approximately 5000 CPS was the maximum even after 10-minute standing. This luminescence intensity was ¼ to ⅙ of that measured from the microbial dissolution solution 1003 that penetrated through the membrane filter and dropped off (FIG. 17). This result demonstrated that only approximately ¼ to ⅙ of the ATP molecules 1501 (FIG. 16A) within the single-layer hydrophilic membrane filter 1001 is liberated into the solution on the hydrophilic membrane filter 1001 (FIG. 16D).

Figure 18:
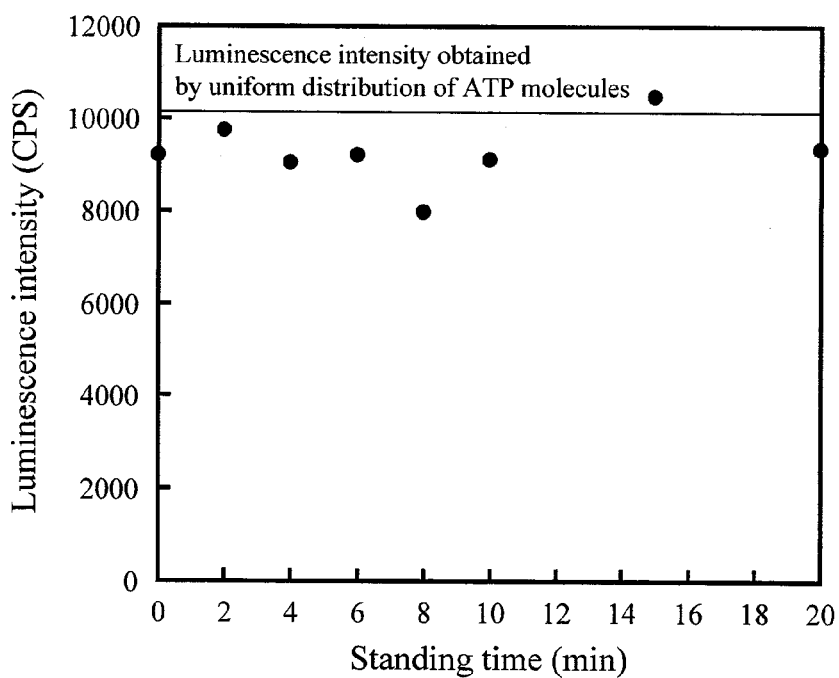
FIG. 18 is a diagram showing time-dependent change in the luminescence intensity of a microbial dissolution solution on the two-layer membrane filter.

On the other hand, the microbial dissolution solution 703 neither penetrated through the two-layer membrane filter 101 nor dropped off. Instead, a 10 μL aliquot was collected from the microbial dissolution solution 703 on the two-layer membrane filter 101 immediately after the addition of the microbial dissolution solution 703 onto the two-layer membrane filter 101 and after 2- to 20-minute standing. The collected solution was subjected to luminescence measurement. At each of the standing times, luminescence intensity was shown to be approximately 9800 CPS (FIG. 18). This result indicates that the ATP molecules 1501 (FIG. 15A) infiltrated in the hydrophilic membrane filter 116 as the first layer can be eluted into the solution on the two-layer membrane filter 101 by retaining the microbial dissolution solution 703 in the container 102 comprising the two-layer membrane filter 101 (FIG. 15D).

This result demonstrated that the ATP molecules 1501 can be eluted efficiently from within the hydrophilic membrane filter 116 as the first layer by retaining the microbial dissolution solution 703 on the two-layer membrane filter 101. The elution can be performed more efficiently by use of the hydrophilic membrane filter as the first layer having a smaller diameter and a smaller thickness.

Experimental Example 4

(Experiment on Measurement of Microbes Using Wetting Agent)

Microbial detection sensitivity was compared between the two-layer membrane filter and a hydrophobic membrane filter capable of filtering an aqueous solution by virtue of a wetting agent infiltrated therein. For this purpose, four containers comprising a membrane filter were prepared.

(1) Container Comprising Two-Layer Membrane Filter:

The two-layer membrane filter comprised a first layer as an upper layer serving as a hydrophilic membrane filter and a second layer as a lower layer serving as a hydrophobic membrane filter. The hydrophilic membrane filter as the first layer used was an MF-Millipore membrane filter (Nihon Millipore Ltd.) having a pore size of 0.45 μm, a thickness of 150 μm, and porosity of 79% and was processed into 0.5 cm in diameter. The hydrophobic membrane filter as the second layer used was a Mitex membrane filter (Nihon Millipore Ltd.) having a pore size of 10 μm and was processed into 0.5 cm in diameter.

(2) Container Comprising Single-Layer Hydrophilic Membrane Filter:

The single-layer hydrophilic membrane filter used was an MF-Millipore membrane filter (Nihon Millipore Ltd.) having a pore size of 0.45 μm, a thickness of 150 μm, and porosity of 79% and was processed into 0.5 cm in diameter.

(3) Container Comprising Wetting Agent-Requiring Two-Layer Membrane Filter which Comprises Hydrophilic Membrane Filter as First Layer and Hydrophobic Membrane Filter Capable of Filtering Aqueous Solution by Virtue of Wetting Agent Infiltrated Therein, as Second Layer:

The hydrophilic membrane filter as the first layer used in the two-layer membrane filter was an MF-Millipore membrane filter (Nihon Millipore Ltd.) having a pore size of 0.45 μm, a thickness of 150 μm, and porosity of 79% and was processed into 0.5 cm in diameter. The hydrophobic membrane filter as the second layer used was a hydrophobic Durapore membrane filter (Nihon Millipore Ltd.) having a pore size of 0.45 μm and was processed into 0.5 cm in diameter.

(4) Container Comprising Wetting Agent-Requiring Single-Layer Hydrophobic Membrane Filter Which Comprises Hydrophobic Membrane Filter Capable of Filtering Aqueous Solution by Virtue of Wetting Agent Infiltrated Therein:

The single-layer hydrophobic membrane filter used was a hydrophobic Durapore membrane filter (Nihon Millipore Ltd.) having a pore size of 0.45 μm and was processed into 0.5 cm in diameter.

*E. coli* was used as the microbe to be measured. *E. coli* was suspended in a phosphate buffer (pH 7.4) (Invitrogen Corp.) to prepare an *E. coli* suspension having 100 individuals of *E. coli*/10 mL. An ATP elimination solution included in the Lucifer HS Set (Kikkoman Corp.) was used as an extra-microbial biological material removal reagent. An ATP extraction solution included in the Lucifer HS Set (Kikkoman Corp.) was used as a microbial dissolution solution.

10 mL of the *E. coli* suspension was added onto each of the two-layer membrane filter, the single-layer hydrophilic membrane filter, the wetting agent-requiring two-layer membrane filter, and the wetting agent-requiring single-layer hydrophobic membrane filter. Then, 10 μm of the ATP elimination solution was added thereto as a first reagent.

The two-layer membrane filter and the single-layer hydrophilic membrane filter could filter the *E. coli* suspension. However, the wetting agent-requiring two-layer membrane filter and the wetting agent-requiring single-layer hydrophobic membrane filter failed to filter the *E. coli* suspension. Therefore, each hydrophobic membrane filter was infiltrated with methyl alcohol as a wetting agent to achieve filtration.

After the filtration, 200 μL of the ATP extraction solution was added thereto as a second reagent. 10 μL of the ATP extraction solution remaining on each of the two-layer membrane filter, the single-layer hydrophilic membrane filter, the wetting agent-requiring two-layer membrane filter, and the wetting agent-requiring single-layer hydrophobic membrane filter was subjected to luminescence measurement.

For the two-layer membrane filter, 140 amol of ATP was detected from 100 individuals of *E. coli*. On the other hand, for the single-layer hydrophilic membrane filter, 10 amol ATP was detected, whereas for the wetting agent-requiring two-layer membrane filter and the wetting agent-requiring single-layer hydrophobic membrane filter, 12 amol of ATP was detected. The number of ATP detected using each membrane filter was approximately 1/10 or less of that detected using the two-layer membrane filter.

This result may be because *E. coli*-derived ATP flowed out during filtration due to damage or dissolution of *E. coli* by the wetting agent infiltrated in the hydrophobic membrane filter.

The microbial detection method which involves filtration through a hydrophobic membrane filter using a wetting agent reduces both microbial detection sensitivity and precision. On the other hand, the two-layer membrane filter without the use of a wetting agent improved microbial detection sensitivity and precision.

DESCRIPTION OF SYMBOLS 101 two-layer membrane filter
102 container
103 reagent supply portion
104 pipe for reagent supply
105 suction portion
106 washing solution supply portion
107 pipe for washing solution supply
108 heating portion
109 arm
110 dispensing portion
111 pipe for dispensing
112 detection portion
113 reaction container
114 input/control portion
115 luminescent reagent
116 hydrophilic membrane filter
117 hydrophobic membrane filter
118 waste liquid portion
301 reagent
302 reagent reservoir
601 excitation light irradiation portion
701 *E. coli*
702 *E. coli* suspension
703 microbial dissolution solution
704 *E. coli*-derived ATP molecules
801 bottom of container
802 annular cap
803 screw
901 screwed bottom of container
902 screwed annular cap
1001 single-layer hydrophilic membrane filter
1002 container
1003 microbial dissolution solution that penetrated through membrane filter and dropped off
1004 *E. coli*-derived ATP molecules that penetrated through membrane filter and dropped off
1101 suction port
1501 ATP molecules
1601 ATP molecules that penetrated through membrane filter and dropped off

What is claimed is:
1. A sample container for a microbial detection process comprising:
a two-layer membrane filter comprising a hydrophilic membrane filter as an upper layer, into which a solution is supplied, and a hydrophobic membrane filter as an underlying lower layer, into which the solution having passed through the hydrophilic membrane filter is supplied; and a container which holds the two-layer membrane filter in a bottom portion where the outer edge of the two-layer membrane filter is secured, wherein the hydrophilic membrane filter has a pore size smaller than that of the hydrophobic membrane filter, wherein the hydrophobic membrane filter is porous membrane filter having a power size of 0.8 μm to 80 μm or a membrane filter having a mesh structure with a pitch size of 1 μm to 59 μm, and wherein the hydrophilic membrane filter has a pore size of 0.05 μm to 0.65 μm.

2. The sample container for the microbial detection process according to claim 1, wherein the pore size of the hydrophilic membrane filter is sized to capture a microbe, and the pore size or pitch size of the hydrophobic membrane filter is sized to retain a reagent.

3. The sample container for the microbial detection process according to claim 1, wherein the hydrophobic membrane filter has a thickness of 7 μm to 800 μm.

4. The sample container for the microbial detection process according to claim 1, wherein the hydrophilic membrane filter has a thickness of 7 μm to 200 μm.

5. The sample container for the microbial detection process according to claim 1, wherein when an aqueous solution is contained in the sample container, and being present above the two layer membrane filter, the aqueous solution can be filtered through the hydrophilic membrane filter and the hydrophobic membrane filter by application of a negative pressure below the hydrophobic membrane filter.

6. A microbial detection apparatus comprising:

a sample container comprising, in a bottom portion thereof, a two-layer membrane filter comprising a hydrophilic membrane filter as an upper layer, into which a solution is supplied, and a hydrophobic membrane filter as an underlying lower layer, into which the solution having passed through the hydrophilic membrane filter is supplied;

a suction portion which forms a negative pressure below the two-layer membrane filter;

a reagent supply portion which separately adds an extra-microbial biological material removal reagent and a microbial dissolution solution to the sample container;

a detection portion which detects luminescence from a sample; and a control portion which controls each portion in the apparatus, the control portion being configured to actuate the reagent supply portion to add the extra-microbial biological material removal reagent to a sample in the sample container, then actuate the suction portion to filter the solution in the sample container through the two-layer membrane filter, and then actuate the reagent supply portion to add the microbial dissolution solution to the sample container, wherein the hydrophilic membrane filter has a pore size smaller than that of the hydrophobic membrane filter, wherein the hydrophobic membrane filter is porous membrane filter having a power size of 0.8 μm to 80 μm or a membrane filter having a mesh structure with a pitch size of 1 μm to 59 μm, and wherein the hydrophilic membrane filter has a pore size of 0.05 μm to 0.65 μm.

7. The microbial detection apparatus according to claim 6, wherein the reagent supply portion supplies a luminescent reagent to the sample container, and the detection portion detects luminescence generated from the solution in the sample container thus supplied with the luminescent reagent.

8. The microbial detection apparatus according to claim 6, further comprising a dispensing portion, wherein the dispensing portion dispenses the microbial dissolution solution to a reaction container, and the detection portion detects luminescence generated through the reaction between the sample solution thus dispensed with the microbial dissolution solution and a luminescent reagent.

9. The microbial detection apparatus according to claim 6, further comprising an excitation light irradiation portion, wherein the detection portion detects fluorescence generated from the sample by excitation light irradiation from the excitation light irradiation portion.

* * * * *